(12) United States Patent
Wlaschin et al.

(10) Patent No.: US 11,779,446 B2
(45) Date of Patent: *Oct. 10, 2023

(54) ORAL COMPOSITIONS AND METHODS OF USE

(71) Applicant: 3M INNOVATIVE PROPERTIES COMPANY, St. Paul, MN (US)

(72) Inventors: Katie F. Wlaschin, St. Paul, MN (US); Amanda C. Engler, Woodbury, MN (US); Hannah C. Cohen, St. Paul, MN (US); Yizhong Wang, Woodbury, MN (US); Tao Gong, Woodbury, MN (US); Tiffany T. Ton, Woodbury, MN (US); Joel D. Oxman, Minneapolis, MN (US); Jie Yang, Woodbury, MN (US); Richard P. Rusin, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/196,872

(22) Filed: Nov. 20, 2018

(65) Prior Publication Data

US 2019/0083220 A1 Mar. 21, 2019

Related U.S. Application Data

(60) Provisional application No. 62/589,278, filed on Nov. 21, 2017.

(51) Int. Cl.
| | |
|---|---|
| A61C 19/06 | (2006.01) |
| A61P 1/02 | (2006.01) |
| A61K 36/00 | (2006.01) |
| A61Q 11/00 | (2006.01) |
| A61K 9/12 | (2006.01) |
| A61K 8/25 | (2006.01) |
| A61K 8/41 | (2006.01) |
| A61K 8/73 | (2006.01) |
| A61K 8/92 | (2006.01) |
| A61K 47/12 | (2006.01) |
| A61K 9/107 | (2006.01) |
| A61K 47/26 | (2006.01) |
| A61K 8/81 | (2006.01) |
| A61K 8/06 | (2006.01) |
| A61K 9/00 | (2006.01) |
| A61K 47/10 | (2017.01) |
| A61K 8/37 | (2006.01) |
| A61K 36/185 | (2006.01) |
| A61K 47/36 | (2006.01) |
| A61K 47/44 | (2017.01) |

(Continued)

(52) U.S. Cl.
CPC ............ *A61C 19/063* (2013.01); *A61K 8/062* (2013.01); *A61K 8/25* (2013.01); *A61K 8/375* (2013.01); *A61K 8/41* (2013.01); *A61K 8/73* (2013.01); *A61K 8/731* (2013.01); *A61K 8/732* (2013.01); *A61K 8/737* (2013.01); *A61K 8/8147* (2013.01); *A61K 8/8176* (2013.01); *A61K 8/922* (2013.01); *A61K 9/006* (2013.01); *A61K 9/0053* (2013.01); *A61K 9/107* (2013.01); *A61K 9/12* (2013.01); *A61K 31/025* (2013.01); *A61K 31/075* (2013.01); *A61K 31/164* (2013.01); *A61K 31/198* (2013.01); *A61K 31/205* (2013.01); *A61K 31/355* (2013.01); *A61K 31/714* (2013.01); *A61K 31/728* (2013.01); *A61K 36/00* (2013.01); *A61K 36/185* (2013.01); *A61K 36/28* (2013.01); *A61K 36/48* (2013.01); *A61K 36/52* (2013.01); *A61K 36/63* (2013.01); *A61K 36/736* (2013.01); *A61K 36/752* (2013.01); *A61K 36/81* (2013.01); *A61K 47/10* (2013.01); *A61K 47/12* (2013.01); *A61K 47/26* (2013.01); *A61K 47/36* (2013.01); *A61K 47/44* (2013.01); *A61P 1/02* (2018.01); *A61Q 11/00* (2013.01)

(58) Field of Classification Search
None
See application file for complete search history.

(56) References Cited

U.S. PATENT DOCUMENTS

| | | | |
|---|---|---|---|
| 4,971,788 A | 11/1990 | Tabibi | |
| 5,130,122 A | 7/1992 | Tabibi | |

(Continued)

FOREIGN PATENT DOCUMENTS

| | | |
|---|---|---|
| GB | 2139919 | 11/1984 |
| GB | 2242358 | 4/1994 |

(Continued)

OTHER PUBLICATIONS

International Search Report for International Application No. PCT/IB2018/059145, dated Mar. 11, 2019.

(Continued)

*Primary Examiner* — Celeste A Roney
(74) *Attorney, Agent, or Firm* — 3M Innovative Properties Company

(57) ABSTRACT

Compositions that include: from 5 wt-% to 30 wt-% of one or more plant based oils based on the total weight of the composition; from 70 wt-% to 95 wt-% of an aqueous phase based on the total weight of the composition; from 0.1 wt-% to 5 wt-% of one or more surfactants based on the total weight of the composition; and from 0.05 wt-% to 3 wt-% of a viscosity modifier, wherein the composition has a pH from 4.5 to 9.5, the composition is an oil in water (o/w) emulsion, and the composition is edible. Methods of utilizing disclosed compositions are also included.

21 Claims, No Drawings

(51) Int. Cl.

| | |
|---|---|
| A61K 36/28 | (2006.01) |
| A61K 36/63 | (2006.01) |
| A61K 31/025 | (2006.01) |
| A61K 31/075 | (2006.01) |
| A61K 31/164 | (2006.01) |
| A61K 31/198 | (2006.01) |
| A61K 31/205 | (2006.01) |
| A61K 31/355 | (2006.01) |
| A61K 31/714 | (2006.01) |
| A61K 31/728 | (2006.01) |
| A61K 36/48 | (2006.01) |
| A61K 36/52 | (2006.01) |
| A61K 36/736 | (2006.01) |
| A61K 36/752 | (2006.01) |
| A61K 36/81 | (2006.01) |

(56) References Cited

U.S. PATENT DOCUMENTS

| | | | |
|---|---|---|---|
| 5,332,595 A * | 7/1994 | Gaonkar | A23D 7/0053 426/601 |
| 5,401,496 A | 3/1995 | Fitzig | |
| 5,618,522 A * | 4/1997 | Kaleta | A61K 8/25 424/60 |
| 6,159,459 A * | 12/2000 | Hunter | A61K 8/73 424/440 |
| 6,596,298 B2 | 7/2003 | Leung | |
| 7,407,669 B2 | 8/2008 | Leung | |
| 7,867,509 B2 | 1/2011 | Leung | |
| 8,460,689 B2 * | 6/2013 | Wlaschin | A61M 16/04 424/405 |
| 8,540,970 B2 | 9/2013 | Rodriguez-Vilaboa | |
| 8,647,608 B2 | 2/2014 | Yang | |
| 8,968,709 B2 | 3/2015 | Yang | |
| 9,289,369 B2 | 3/2016 | Boyd | |
| 9,458,414 B2 * | 10/2016 | Rieth | C11D 3/2096 |
| 9,724,278 B2 | 8/2017 | Lambert | |
| 2005/0281772 A1 * | 12/2005 | Bromley | A61P 13/02 424/70.14 |
| 2006/0088482 A1 | 4/2006 | Wulknitz | |
| 2006/0263412 A1 | 11/2006 | Pan | |
| 2007/0031561 A1 | 2/2007 | Lakkis | |
| 2007/0154411 A1 * | 7/2007 | Barth | A61K 8/19 424/50 |
| 2007/0183985 A1 | 8/2007 | Tallia | |
| 2007/0190090 A1 | 8/2007 | Brown | |
| 2008/0020024 A1 | 1/2008 | Kulkarni | |
| 2009/0311200 A1 | 12/2009 | Lambert | |
| 2010/0098791 A1 | 4/2010 | Rodriguez-Vilaboa | |
| 2010/0233221 A1 | 9/2010 | Folmer | |
| 2011/0104081 A1 * | 5/2011 | Scott | A61K 8/86 424/53 |
| 2013/0052146 A1 | 2/2013 | Yang | |
| 2013/0269133 A1 | 10/2013 | Ontumi | |
| 2014/0155457 A1 * | 6/2014 | Nho | A61K 31/77 514/425 |

FOREIGN PATENT DOCUMENTS

| | | |
|---|---|---|
| WO | WO 95/023583 A1 | 9/1995 |
| WO | WO 99/29686 | 6/1999 |
| WO | WO 2012/087279 | 6/2012 |
| WO | WO 2012/087280 | 6/2012 |
| WO | WO 2012/087281 | 6/2012 |

OTHER PUBLICATIONS

Zhang, "Food-grade filled hydrogels for oral delivery of lipophilic active ingredients: Temperature-triggered release microgels", *Food Research International*, 2015, 69:274-280.

Kelly, H.M., et al. "Bioadhesive, Rheological, Lubricant and Other Aspects of an Oral Gel Formulation Intended for the Treatment of Xerostomia," International Journal of Pharmaceutics, 278 (2004), pp. 391-406. © 2004 Elsevier B.V.

Donaldson, et al., *Xerostomia Treatment: A Systematic Approach to Xerostomia Diagnosis and Management*, Jan. 2019, Compendium eBook Continuing Education, AEGIS Publications LLC, 10 pages.

Donaldson, *Xerostomia Update: Comprehensive and Systematic Diagnosis and Management*, Jan. 2020, CDE World eBook, Continuing Dental Education, Dental Learning Systems, LLC, vol. 7, No. 158, 16 pages.

Furness, et al., "Interventions for the management of dry mouth: topical therapies (Review)", 2011, *The Cochrane Library*, Issue 12, The Cochrane Collaboration, John Wiley & Sons, Ltd., 106 pages.

* cited by examiner

ORAL COMPOSITIONS AND METHODS OF USE

TECHNICAL FIELD

The present disclosure relates to oral compositions, and more specifically oral compositions and methods to relieve xerostomia and improve oral health of a subject.

BACKGROUND

Xerostomia or dry mouth is a common condition that results from insufficient saliva volume. It is increasingly prevalent in the aging population and is a side-effect of many medications, as well as cancer treatment. Severe cases of xerostomia are often related to salivary gland dysfunction, known as Sjögren's Syndrome.

The lack of moisture and lubrication typically provided by saliva has a range of negative effects on oral tissue (soft tissue) ranging from mild discomfort to extremely painful and infected mouth sores. The persistent discomfort and dryness can also contribute to larger health issues by causing disruption of sleep, and impairing one's ability to talk (socialize, may impact psychological health) and eat (may impact nutrition). Dry buccal tissue is a less effective barrier and more susceptible to penetration by physical irritants such as toxins and carcinogens in foods, beverages and tobacco. There remains a need for compositions which provide improved relief for xerostomia.

SUMMARY

Disclosed herein are oil in water compositions that include: from 5 wt-% to 30 wt-% of one or more plant based oils based on the total weight of the composition; from 70 wt-% to 95 wt-% of an aqueous phase; from 0.1 wt-% to 5 wt-% total of one or more surfactants; from 0.05 wt % to 3 wt-% total of one or more viscosity modifiers. The surfactants include (i) nonionic surfactants which are ethylene oxide/propylene oxide (EO/PO) free, or (ii) surfactants of formula I:

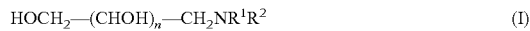

$$HOCH_2-(CHOH)_n-CH_2NR^1R^2 \quad (I)$$

wherein $R^1$ and $R^2$ are independently selected from the group consisting of a hydrogen atom, an alkyl group, $C(O)R^3$, and $SO_2R^4$; with $R^3$ and $R^4$ being independently selected from the group consisting of an alkyl group, an aryl group, and an aralkyl group; wherein n is an integer from about 2 to about 5; or combinations of surfactants from surfactant group (i) and surfactant group (ii). The viscosity modifier is selected from the group consisting of an edible polymeric viscosity modifier, a silica containing viscosity modifier and combinations thereof. The composition also has a pH from 4.5 to 9.5 and is edible.

Also disclosed are compositions wherein the viscosity modifier comprises fumed silica present in an amount equal to or greater than 0.5 wt-%. based on the total weight of the composition.

Also disclosed are compositions wherein the one or more ethylene oxide/propylene oxide (EO/PO) free, nonionic surfactants is a polyglycerol ester surfactant.

Also disclosed are methods of preventing, inhibiting, disrupting, or any combination thereof the formation or maintenance of a biofilm in an oral tissue, the methods including contacting an oral tissue with disclosed compositions.

Also disclosed are methods of affecting hydration loss in an oral tissue, the methods including contacting an oral tissue with disclosed compositions.

Also disclosed are methods of affecting lubricity or lubriciousness in an oral tissue, the methods including contacting an oral tissue with disclosed compositions.

Also disclosed are methods of affecting the effects of xerostomia, dry mouth, or both, the methods including contacting an oral tissue with disclosed compositions.

The above summary is not intended to describe each embodiment of the present disclosure. The details of one or more embodiments of the present disclosure are also set forth in the description below. Other features, objects, and advantages of the present disclosure will be apparent from the description and from the claims.

DETAILED DESCRIPTION

Saliva is the mouth's primary defense against tooth decay. Healthy saliva flow helps prevent cavities by physically removing bacteria from the oral cavity before they can become attached to tooth and tissue surfaces and form a protected biofilm. The flow of saliva also helps dilute sugars and acids introduced by intake of food and beverages. The buffering capacity neutralizes acids and aids in the digestive process. The presence of calcium and phosphate salts provides continuous opportunity for re-mineralization of tooth enamel, serving to reverse the tooth decay process.

Many who suffer with xerostomia use separate products to address hard tissue health and soft tissue comfort. For soft tissue comfort, saliva substitute products are typically designed to provide lubrication and moisture. The format of these products is varied, and includes viscous gels/pastes, sprays, rinses, mints, and slow-release tablets. These are applied multiple-times per day or as needed for comfort. For hard-tissue health, different treatments are used to directly address cavity prevention (antiseptic rinses, fluoride products, calcium/phosphate treatments). Often "dry mouth-friendly" versions of products, such as toothpastes and mouth rinses are recommended. Dry mouth friendly products typically have a neutral pH and do not contain alcohol or other irritating components (e.g. anionic surfactants or emulsifiers).

There is a desire to design a single product that effectively addresses both the need for dry mouth symptom relief (soft tissue comfort) and oral health preventative benefits (tooth enamel and cavity protection). A fully ingestible, two-phase emulsion system is well suited for this purpose. It addresses both the health of hard-tissue (water phase) and soft tissue (oil phase).

Disclosed herein are compositions that can be utilized as oral compositions, for example. Disclosed compositions are oil-in-water (o/w) emulsions. An o/w (oil-in-water) emulsion consists of oil droplets dispersed in a continuous aqueous phase. In some embodiments, useful compositions can be characterized as a macroemulsion. Macroemulsions are kinetically stabilized mixtures of at least two immiscible liquids where one of the liquids has droplets with a diameter greater than 0.1 μm. Macroemulsions scatter light effectively and therefore appear milky, because their droplets are greater than a wavelength of light.

Disclosed compositions, one or more components in a composition, or both can be characterized as edible. Referring to a component or composition as edible can mean that the particular ingredient or composition is safe for daily, long-term ingestion at recommended use levels. In some embodiments, the GRAS (generally regarded as safe) list from the United States Food and Drug Administration (FDA) can be utilized to determine if a component is edible at the levels utilized in a composition.

Disclosed compositions include at least water, oil, surfactant, and a viscosity modifier. The amount of water in disclosed compositions can be characterized by the amount of aqueous phase in the composition. The aqueous phase can include components other than water, for example it can include components that are soluble in water (as opposed to the oil phase). In some embodiments, the aqueous phase can be not less than 70 percent by weight (wt-%) based on the total weight of the composition, not less than 75 wt-% based on the total weight of the composition, or not less than 78 wt-% based on the total weight of the composition. In some embodiments, the aqueous phase can be not greater than 95 wt-% based on the total weight of the composition, not greater than 92 wt-% based on the total weight of the composition, not greater than 90 wt-% based on the total weight of the composition, or not greater than 89.5 wt-% based on the total weight of the composition.

Disclosed compositions also include one or more oils. Useful oils can include any oils but in some embodiments can include plant based oils. For example, plant based oils can be extracted from various plants (e.g., soybean, canola, and chili), seeds (e.g., sesame and sunflower), nuts (e.g., walnut and macadamia), and fruits (e.g., palm, olive, and coconut), for example. In some embodiments, useful oils can include one or more than one that are liquids at room temperature. The composition can include a single edible oil, or as many as two, three, four, five or more edible oils. Examples of suitable edible oils can include, but are not limited to, sunflower oil (including high oleic sunflower oil), safflower oil (including high oleic safflower oil), olive oil, coconut oil, palm oil, peanut oil, soybean oil, linseed oil, rapeseed oil, flaxseed oil, hempseed oil, cocoa butter, walnut oil, corn oil, grape seed oil, sesame oil, groundnut oil, wheat germ oil, cottonseed oil, fish oil, watermelon seed oil, lemon oil, orange oil, thistle oil, tomato seed oil, almond oil, *perilla* oil, canola oil, pistachio oil, hazelnut oil, avocado oil, ozonated oils, and the like, and mixtures or fractions thereof. Disclosed compositions can include not less than 15 wt-% of one or more oil, not less than 12 wt-% of one or more oil based on the total weight of the composition, not less than 10 wt-% of one or more oil based on the total weight of the composition, or not less than 5 wt-% of one or more oils based on the total weight of the composition. Disclosed compositions can include not greater than 30 wt-% of one or more oil based on the total weight of the composition, not greater than 25 wt-% of one or more oil based on the total weight of the composition, or not greater than 22 wt-% of one or more oil based on the total weight of the composition.

Disclosed compositions also include one or more surfactants. In some embodiments, disclosed compositions include nonionic surfactants. In some embodiments, compositions include edible nonionic surfactants. In some embodiments, the surfactants are ethylene oxide/propylene oxide (EO/PO) free surfactants. EO/PO based or EO/PO-containing surfactants and polymers may have 1,4 dioxane contamination and are therefore not advantageous for ingestion and especially not long-term ingestion.

In some embodiments, useful surfactants can include glycerol ester and polyglycerol ester surfactants, for example. Glycerol ester and Polyglycerol ester surfactants can be derived from natural sources, can be 1,4 dioxane free, and can be renewable. Polyglycerol ester surfactants are a class of ester emulsifiers that can have a wide range of hydrophilic-lipophilic characteristics and can be made from raw materials of 100% plant origin. These non-ionic emulsifiers are highly compatible with many different chemicals, and other co-emulsifiers, helping to create stable oil-in-water emulsions. Furthermore, Polyglycerol esters are ECO-CERT approved, making them an advantageous choice for natural concepts and PEG-free formulations.

Polyglycerol ester emulsifiers can be formed chemically by esterification of fatty acids, largely saturated or mono-unsaturated, to one or several hydroxyl groups of polyglycerol. As glycerol is a trifunctional molecule, it may condense with itself to give oligomer and polymers. These polyglycerols are hydroxy-containing ethers, diglycerol being the simplest example. If the primary hydroxyls are the only ones concerned in the reaction, the products are linear, but if the secondary hydroxyl groups are also involved, branched chains are formed. Thus, several diglycerol molecules can be formed, but if the polymerization proceeds to tri-, tetra- and higher glycerols the number of possible isomers increases exponentially to form many different linear isomers. Classically, 30 to 50% of the total amount of hydroxyl groups are esterified by fatty acids. These fatty acids are formed either of one species (such as lauric, stearic or oleic acid) or a mixture of these from oil. Chemically, polyglycerol esters may be formed by an alkaline catalyzed random polymerization of glycerol followed by an esterification with isolated fatty acids or triacylglycerols. The obtained mixture varies in polymerization degree, kind and position of esterified fatty acid (monoesters diglycerol or triglycerol or tetraglycerol, diesters diglycerol or triglycerol). These surfactants, made via esterification of a polyglycerol and a fatty acid, form a molecule which contains a hydrophilic head group and hydrophilic tail group. The physical properties and appearance of polyglyceryl esters of fatty acids mainly depends on their molecular structure. Typically, the physical form of those with a higher degree of polymerization and shorter or unsaturated fatty acid chains ranges from viscous liquids to plastic pastes, and the polyglyceryl esters with a lower degree of polymerization and longer, saturated fatty acid chains are generally powders, flakes or small beads. The color of the esters is dependent on the source of the fatty acids, but the polyglycerol will contribute to the color. The solubility of polyglyceryl esters in organic solvents depends on the nature of the solvent and the polarity of the ester but, generally, the esters will show best solubility in protic and polar aprotic solvents, such as lower alcohols and dimethyl sulfoxide. Polyglyceryl esters of fatty acids are polar or amphiphilic lipids, and the amphiphilic properties in water exhibit mesomorphic activities forming lyotropic liquid crystals. The polyglyceryl ester as a polar emulsifier will form aggregated bodies, such as micelles, at low concentrations in water. Polyglyceryl esters are important non-ionic surfactants with various applications in cosmetic, food, pharmaceutical and other industries. Their amphiphilic character enables their use in the stabilization of various suspensions. In foods industry, they are used as emulsifying agents in the production of fine bakery in replacement of fats. Thus, polyglycerol polyricinoleate, is an emulsifier made from castor beans which reduces the viscosity of chocolate and similar coatings and compounds.

Traditional emulsifiers, such as EO/PO polymer-based esters and sorbitan esters, are popular because of their ability to create stable formulations and their ease of use. They were created when ingredients made from raw materials like ethylene oxide which were not well researched and were generally accepted by the public. Today, consumers are more educated and are moving away from these types of chemistries because of the utilization of ethylene oxide and the potential to contain residual 1,4 dioxane, a well-researched carcinogen.

POLYALDO® Polyglyceryl Esters from Lonza are different from traditional EO/PO based emulsifier. POLYALDO® Polyglyceryl Esters are 100% vegetable origin. Polyglycerol ester product manufactured by Lonza has a three-character suffix, beginning with two numerical values and ending with a letter of the Roman alphabet. The first numerical value represents the degree of polymerization of the polyglycerol molecule. It is the number of glycerin units which have been reacted with each other to form the polyglycerol chain. The second numerical value represents the degree of esterification of the polyglyceryl ester. It is the number of fatty acid molecules which have been reacted with the polyglycerol chain. The last character is a letter of the Roman alphabet. This represents the type of fatty acid used in the esterification process. The POLYALDO polyglycerol esters utilizes stearic, oleic, palmitic, and lauric acid as the fatty acids of interest. Here is an example of Lonza polyglycerol ester emulsifier, POLYALDO® 6-2-S (INCI: Polyglyceryl-6 Distearate). The suffix for this product contains a "6", a "2", and the letter "S". Based on the nomenclature guidelines above, the characters represent the following: 6 is a polyglycerol made up of six (6) units of glycerin. 2 is the degree of esterification that is two (2) and is reflected in the fatty acid as a "distearate". S is stearic acid that is used as the fatty acid for esterification. POLYALDO®10-1-S (INCI: Polyglyceryl-10 Stearate). The suffix for this product contains a "10", a "1", and the letter "S". Based on the nomenclature guidelines above, the characters represent the following: 10 is a polyglycerol made up of ten (10) units of glycerin. 1 is the degree of esterification that is one (1) and is reflected in the fatty acid as a "stearate". S is stearic acid that is used as the fatty acid for esterification. These naturally-derived plant-based emulsifiers provide an EO/PO-free option and an alternative to PEG-based chemistries.

In some embodiments, useful surfactants can include those of formula I:

$$HOCH_2—(CHOH)_n—CH_2NR^1R^2 \quad (I)$$

wherein $R^1$ and $R^2$ are independently selected from the group consisting of a hydrogen atom, an alkyl group, $C(O)R^3$, and $SO_2R^4$; with $R^3$ and $R^4$ being independently selected from the group consisting of an alkyl group, an aryl group, and an aralkyl group; and n is an integer from about 2 to about 5.

The groups $R^1$ and $R^2$ are independently selected from the group consisting of a hydrogen atom, an alkyl group, $C(O)R^3$, and $SO_2R^4$. Each of $R^1$ and $R^2$ may be a hydrogen atom, each of $R^1$ and $R^2$ may be an alkyl group, each of $R^1$ and $R^2$ may be $C(O)R^3$, or each of $R^1$ and $R^2$ may be $SO_2R^4$. In some embodiments, $R^1$ may be a hydrogen atom and $R^2$ may be an alkyl group, $C(O)R^3$, or $SO_2R^4$. In other embodiments, $R^1$ may be an alkyl group, and $R^2$ may be $C(O)R^3$, or $SO_2R^4$. In still other embodiments, $R^1$ may be $C(O)R^3$, and $R^2$ may be $SO_2R^4$. When either or both of $R^1$ and $R^2$ is an alkyl group, the alkyl group may comprise about one carbon atom, more than about one carbon atom, more than about two carbon atoms, more than about four carbons atoms, more than about six carbon atoms, more than about eight carbon atoms, more than about ten carbon atoms, more than about twelve carbon atoms, more than about fourteen carbon atoms, more than about sixteen carbon atoms, or more than about eighteen carbon atoms. In some embodiments, the alkyl group comprises less than about thirty carbon atoms, less than about twenty-six carbon atoms, or less than about twenty carbon atoms. In some embodiments, the alkyl group comprises a straight chain alkyl group. In other embodiments, the alkyl group comprises a branched alkyl group. In still other embodiments, the alkyl group comprises a cyclic alkyl group. When each of $R^1$ and $R^2$ comprises an alkyl group, $R^1$ and $R^2$ may comprise the same alkyl group, or $R^1$ and $R^2$ may comprise different alkyl groups. Non-limiting examples of alkyl groups include methyl, ethyl, 1-propyl, iso-propyl, butyl, iso-butyl, sec-butyl, pentyl, iso-pentyl, neo-pentyl, hexyl, 2-ethylhexyl, octyl, decyl, undecyl, dodecyl, tetradecyl, pentadecyl, octadecyl, cyclohexyl, 4-methylcyclohexyl, cyclohexylmethyl, cyclopenyl, and cyclooctyl.

The groups $R^3$ and $R^4$ are independently selected from the group consisting of an alkyl group, an aryl group, and an aralkyl group. When either or both of $R^3$ or $R^4$ is an alkyl group, the alkyl group may comprise about one carbon atom, more than about one carbon atom, more than about two carbon atoms, more than about four carbons atoms, more than about six carbon atoms, more than about eight carbon atoms, more than about ten carbon atoms, more than about twelve carbon atoms, more than about fourteen carbon atoms, more than about sixteen carbon atoms, or more than about eighteen carbon atoms. In some embodiments, the alkyl group comprises less than about thirty carbon atoms, less than about twenty-six carbon atoms, or less than about twenty carbon atoms. In some embodiments, the alkyl group comprises a straight chain alkyl group. In other embodiments, the alkyl group comprises a branched alkyl group. In still other embodiments, the alkyl group comprises a cyclic alkyl group. In compounds of Formula I or pharmaceutically acceptable salts thereof, when both $R^3$ and $R^4$ groups are present, and when each of $R^3$ and $R^4$ comprises an alkyl group, $R^3$ and $R^4$ may comprise the same alkyl group, or $R^3$ and $R^4$ may comprise different alkyl groups. Non-limiting examples of alkyl groups include methyl, ethyl, 1-propyl, iso-propyl, butyl, iso-butyl, sec-butyl, pentyl, iso-pentyl, neo-pentyl, hexyl, 2-ethylhexyl, octyl, decyl, undecyl, dodecyl, tetradecyl, pentadecyl, octadecyl, cyclohexyl, 4-methylcyclohexyl, cyclohexylmethyl, cyclopenyl, and cyclooctyl.

When either or both of $R^3$ or $R^4$ are an aryl group, the aryl group may comprise one arene ring or more than one arene ring. Arene rings may comprise up to six carbon atoms, up to eight carbon atoms, up to ten carbon atoms, up to twelve carbon atoms, up to fourteen carbon atoms, up to sixteen carbon atoms, or up to eighteen carbon atoms. Arene rings may comprise a heteroatom, for example, nitrogen, oxygen, or sulfur. If more than one arene ring is present, the arene rings may be fused together, or they may be joined by a chemical bond. In compounds of Formula I or pharmaceutically acceptable salts thereof, when both $R^3$ and $R^4$ groups are present, and when each of $R^3$ and $R^4$ comprises an aryl group, $R^3$ and $R^4$ may comprise the same aryl group, or $R^3$ and $R^4$ may comprise different aryl groups. Non-limiting examples of aryl groups include substituted and unsubstituted phenyl, 1-naphthyl, 2-naphthyl, 9-anthracenyl.

When either or both of $R^3$ or $R^4$ are an aralkyl group, the aralkyl group may comprise one arene ring or more than one arene ring. The aralkyl group may comprise up to six carbon atoms, up to eight carbon atoms, up to ten carbon atoms, up to twelve carbon atoms, up to fourteen carbon atoms, up to sixteen carbon atoms, up to eighteen carbon atoms, or up to twenty carbon atoms. If more than one arene ring is present in the aralkyl group, the arene rings may be fused together, or they may be joined by a chemical bond. Arene rings may comprise a heteroatom, for example, nitrogen, oxygen, or sulfur. In compounds of Formula I or pharmaceutically acceptable salts thereof, when both $R^3$ and $R^4$ groups are present, and when each of $R^3$ and $R^4$ comprises an aralkyl group, $R^3$ and $R^4$ may comprise the same aralkyl group, or $R^3$ and $R^4$ may comprise different aralkyl groups. Non-limiting examples of aralkyl groups include benzyl, 1-phenylethyl, 2-phenylethyl, 3-phenylpropyl, 2-naphthylethyl, and 9-anthracenylmethyl.

In Formula I, n is an integer from about 2 to about 5. In some embodiments, the dental composition comprises a compound of Formula I, or a pharmaceutically acceptable salt thereof, wherein n is an integer having a value of about 5, about 4, about 3, or about 2. In some embodiments, n is an integer having a value of 5, or 4, or 3, or 2. It is understood that the dental composition may comprise more than one compound of Formula I, or a pharmaceutically acceptable salt thereof, and that the compounds may be represented by Formula I with different integer values of n. In these embodiments, the average value of n of a composition may be a non-integer.

It is recognized that the compounds of Formula I include chiral carbon atoms. For simplicity, in Formula I, the stereochemical configuration about each of the chiral carbon atoms is not specified. It is intended that FormulasI, as used in this description and in the claims, represents each of the compounds having any of the possible stereochemical configurations. In some embodiments, the compounds of Formula I are amino sugar alcohols and derivatives having the common names D-glucamine, N-methyl-D-glucamine, N-ethyl-D-glucamine, N-octyl-D-glucamine, and N-methyl-N-octanoyl-D-glucamine, N-methyl-N-nonanoyl-D-glutamine, N-methyl-N-decanoyl-D-glucamine. Many of the compounds of Formula I are commercially available. For example, N-methyl-N-nonanoyl-D-glucamine ("MEGA-9") is commercially available from EMD Chemicals, Inc. (San Diego, Calif.).

Pharmaceutically acceptable salts of compounds of Formula I can also be utilized and can include ammonium salts. In some embodiments, the dental composition of the invention comprises an ammonium salt. An ammonium salt may be represented as the reaction product of an acid with an amine, or as the reaction product of an amine with an alkylating agent such as, for example, iodomethane, bromoethane, or benzyl bromide. An ammonium salt includes a protonated amine compound, for example a compound of Formula I in which a $NR^1R^2$ group, wherein $R^1$ and $R^2$ are independently selected from the group consisting of a hydrogen atom and an alkyl group, has been protonated with an inorganic acid or an organic acid. An ammonium salt includes an alkylated amine compound, for example a compound of Formula I in which a $NR^1R^2$ group, wherein $R^1$ and $R^2$ are independently selected from the group consisting of a hydrogen atom and an alkyl group, has been alkylated with an alkylating agent.

An ammonium salt comprises at least one counter ion that may be an inorganic anion, an organic anion, or a combination of anions. A combination of anions includes a combination of more than one inorganic anion, a combination of more than one organic anion, or a combination of an inorganic ion and an organic anion. Inorganic ions include, for example, halide (fluoride, chloride, bromide, and iodide), nitrate, sulfate, tetrafluroborate, and tetra(aryl)borates. Tetra (aryl)borates include compounds having the formula $Z_4B^-$, where Z is an aromatic group, for example a substituted or unsubstituted phenyl group. Examples of tetra(aryl)borates include, but are not limited to, tetraphenylborate, tetrakis(4-methylphenyl)borate, tetrakis(2-methylphenyl)borate, tetrakis(1,3,5-trimethylphenyl)borate, tetrakis(4-fluorophenyl)borate, tetrakis(pentafluorophenyl)borate, and tetrakis(4-trifluoromethylphenyl)borate. Organic anions include, for example, alkanoates (such as, for example, acetate, propionate, and butanoate), benzoate, fumarate, maleate, tartrate, ascorbate, benzenesulfonate, toluenesulfonate, and citrate. In some embodiments, the pharmaceutically acceptable salt is free of unsubstituted or substituted tropolone.

In certain implementations, an ammonium salt may be formed by protonation of a compound of Formula I, wherein $R^1$ and $R^2$ are independently selected from a hydrogen atom and an alkyl group, with an inorganic acid, an organic acid, or a combination of an inorganic acid and an organic acid. In another embodiment, an ammonium salt may be formed by alkylation of a compound of Formula I, wherein $R^1$ and $R^2$ are independently selected from a hydrogen atom and an alkyl group, with an alkylating agent. In yet another embodiment, an ammonium salt may be formed by an ion exchange or metathesis reaction with a previously formed ammonium salt. In some embodiments, $R^1$ comprises an alkyl group and $R^2$ is $C(O)R^3$, where $R^3$ comprises an alkyl group. In certain embodiments, $R^1$ comprises an alkyl group having from about one to about four carbon atoms, and $R^3$ comprises an alkyl group having from about four to about sixteen carbon atoms. In some embodiments, $R^1$ comprises a methyl group, and $R^3$ comprises an alkyl group having seven, eight, or nine carbon atoms. In some embodiments, the dental composition comprises a compound of Formula III, Formula IV, or Formula V.

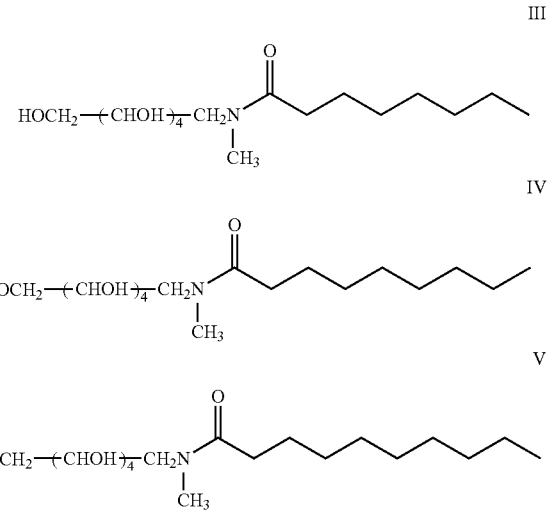

Disclosed compositions can include not greater than 5 wt-% of one or more surfactants based on the total weight of the composition, not greater than 4.5 wt-% of one or more surfactants based on the total weight of the composition, or not greater than 4 wt-% of one or more surfactants based on the total weight of the composition. In some embodiments, disclosed composition can include not less than 0.5 wt-% of one or more surfactants based on the total weight of the composition, not less than 0.4 wt-% of one or more surfactants based on the total weight of the composition, or not less than 0.3 wt-% of one or more surfactants based on the total weight of the composition.

Disclosed compositions also include one or more viscosity modifying agents. In some embodiments, disclosed compositions can include polymeric viscosity modifying agents. Illustrative useful polymeric viscosity modifying agents can include, for example hydroxypropyl guar, xanthan gum, iota carrageenan, or combinations thereof. In some embodiments, combinations of at least two of hydroxypropyl guar, xanthan gum, and ethylcellulose can be utilized. In some embodiments, various molecular weights of any of xanthan gum, hydroxypropyl guar, and ethylcellulose can be utilized, for example. In some embodiments, disclosed compositions that include polymer viscosity modifying agents can include not greater than 3 wt-% of one or more polymer viscosity modifying agents based on the total weight of the composition, not greater than 2 wt-% of one or more polymer viscosity modifying agents based on the total weight of the composition, or not greater than 1.5 wt-% of one or more polymer viscosity modifying agents based on the total weight of the composition. In some embodiments, disclosed compositions that include polymer viscosity modifying agents can include not less than 0.2 wt-% of one or more polymer viscosity modifying agents based on the total weight of the composition, not less than 0.1 wt-% of one or more polymer viscosity modifying agents based on the total weight of the composition, or not less than 0.05 wt-% of one or more polymer viscosity modifying agents based on the total weight of the composition. In some embodiments, disclosed compositions can include silica-containing viscosity modifying agents. In some embodiments, such viscosity modifying agents can include fumed silica, or precipitated silica for example. In some embodiments, disclosed compositions that include silica-containing viscosity modifying agents can include not greater than 2 wt-% of one or more silica-containing viscosity modifying agents based on the total weight of the composition, or not greater than 1.5 wt-% of one or more silica-containing viscosity modifying agents based on the total weight of the composition.

Disclosed compositions can also optionally include additional components other than water, one or more oils, one or more surfactants and one or more viscosity modifying agents. Illustrative optional components can include, for example, sweeteners, humectants, mineral salts, buffering components, flavorants, preservative agents, tooth re-mineralizing agents, dental caries preventing agents, or combinations thereof. Other optional beneficial ingredients can also be included at appropriate levels such as, aloe vera (multi-benefit), folic acid (related to B12), hyaluronic acid (lubricating, healthy skin), ceramides (healthy skin), arginine, betaines or oxygenated glycerol triesters, vitamin E (antioxidant and preservative), vitamin B12 (healthy skin, etc.), EDTA, cetyl pyridinium chloride, chlorhexidine, other antiseptics, etc., or combinations thereof.

In some embodiments, disclosed compositions can include flavorants including for example, peppermint, strawberry, butter, vanilla, coconut, almond, bubble gum, berry, fruit punch, butterscotch, caramel, or combinations thereof. In some embodiments, some flavorants, e.g., mint, citrus, etc. can also be advantageous because they stimulate salivary production when utilized in compositions. Artificial sweeteners may also be used (stevia, aspartame, sucralose, neotame, acesulfame potassium (Ace-K), saccharin, and advantame, for example). In some embodiments, disclosed compositions can include one or more sweeteners including for example, non-cariogenic polyols, or sugar substitutes (e.g., sucralose). In some embodiments, disclosed compositions can include non-cariogenic polyol sweeteners such as xylitol, sorbitol, maltitol, erythritol, isomalt, or combinations thereof. In compositions that include optional sweeteners, the sweetener can be present in an amount that is not less than 2.5 wt-% based on the total weight of the composition or not less than 1 wt-% based on the total weight of the composition. In some embodiments, an optional sweetener can be present in an amount that is not greater than 35 wt-% based on the total weight of the composition or not greater than 20 wt-% based on the total weight of the composition or not greater than 15 wt-% based on the total weight of the composition.

In some embodiments, disclosed compositions can include one or more humectants including for example glycerin, propylene glycol, or sucrose, or combinations thereof. In some embodiments, disclosed compositions can include one or more humectants including for example glycerin, propylene glycol, sucrose or combinations thereof. In compositions that include optional humectants, the one or more humectant can be present in an amount of not less than 2.5 wt-% based on the total weight of the composition, not less than 5 wt-% based on the total weight of the composition, or not less than 10 wt-% based on the total weight of the composition. In compositions that include optional humectants, the one or more humectant can be present in an amount of not greater than 40 wt-% based on the total weight of the composition, not greater than 35 wt-% based on the total weight of the composition, or not greater than 30 wt-% based on the total weight of the composition.

In various embodiments, disclosed compositions can further include one or more tooth re-mineralizing agents alone or in combination with one or more minerals that may be useful or beneficial for ingestion or oral health.

In some embodiments, disclosed compositions can optionally include one or more minerals that may be useful or beneficial for ingestion or oral health. Illustrative optional minerals that can be included in disclosed compositions can include calcium (Ca), phosphorus (P), magnesium (Mg), fluorine (F), iron (Fe), strontium (Sr), zinc (Zn), potassium (K), or combinations thereof. In some embodiments, some minerals can be provided by including magnesium chloride ($MgCl_2$), calcium chloride ($CaCl_2$)), strontium chloride, zinc chloride, zinc gluconate, potassium nitrate, potassium phosphate dibasic ($KH_2PO_4$), or combinations thereof. In some embodiments, where fluorine is included, it can be included as the fluoride ion (F—) in salt form ($MgF_2$, $CaF_2$, etc.), at a concentration that is not greater than 4 milligrams per liter (mg/L).

In particular, some calcium containing compounds are particularly advantageous to include in the disclosed compositions. Such calcium compounds include: calcium chloride, calcium carbonate, calcium caseinate, calcium citrate, calcium glubionate, calcium gluceptate, calcium glycerophosphate, calcium gluconate, calcium hydroxide, calcium hydroxyapatite, calcium lactate, calcium oxalate, calcium oxide lime, calcium pantothenate, dibasic and tribasic calcium phosphate, calcium polycarbophil, calcium propionate, calcium pyrophosphate, and calcium sulfate. These compounds have been found to minimize demineralization of calcium hydroxyapatite at the surface of the tooth of a patient.

In some embodiments, the tooth re-mineralizing agents (compounds) include phosphate compounds. Suitable phosphate compounds include, but are not limited to, aluminum phosphate, bone phosphate, calcium phosphate, calcium orthophosphate, calcium phosphate dibasic anhydrous, calcium phosphate-bone ash, calcium phosphate dibasic dihydrate, calcium phosphate dibasic anhydrous, calcium phosphate dibasic dihydrate, calcium phosphate tribasic, dibasic calcium phosphate dihydrate, dicalcium phosphate, neutral calcium phosphate, calcium orthophosphate, tricalcium phosphate, precipitated calcium phosphate, tertiary calcium phosphate, whitlockite, magnesium phosphate, potassium phosphate, dibasic potassium phosphate, dipotassium hydrogen orthophosphate, dipotassium monophosphate, dipotassium phosphate, monobasic potassium phosphate, potassium acid phosphate, potassium biphosphate, potassium dihydrogen orthophosphate, potassium hydrogen phosphate, sodium phosphate, anhydrous sodium phosphate, dibasic sodium phosphate, disodium hydrogen orthophosphate, disodium hydrogen orthophosphate dodecahydrate, disodium hydrogen phosphate, disodium phosphate, and mixtures and combinations thereof.

In some embodiments, the calcium compounds, phosphate compounds, or both, are present in the inventive composition in an amount sufficient such that the composition is saturated with at least one of $Ca^{2+}$ ions and $PO_4^{3-}$ ions. In some embodiments, saturated with at least one of calcium ion or phosphate ion can substantially reduce or prevent demineralization, or enhance remineralization, or both, on the surface of the teeth of the patient.

In various embodiments, the tooth re-mineralizing agent is present at up to about 1 part by weight, or up to about 2 parts by weight, or up to about 5 parts by weight.

In some embodiments, disclosed compositions can include one or more preservatives to render the composition microbiologically stable, to increase the microbiological stability thereof, or some combination thereof. In some embodiments, useful preservatives include those that work at a neutral pH, do not detrimentally affect taste, are edible, are effective against a broad spectrum of pathogens, or combinations thereof. Specific illustrative useful preservatives can include GEOGARD® preservatives, which are commercially available from Lonza (Basel, Switzerland) and include benzyl alcohol, sodium benzoate, potassium sorbate, parabens, natural preservatives, polyglyceryl esters, monolaurin, 1,2 octanediol, caprylic/capric triglycerides, DHA, aloe vera, potassium sorbate, CPC, PHMB, CHG, vitamin E, triethyl citrate, and EDTA, for example.

In some embodiments, disclosed compositions can include one or more naturally occurring amino acids as agents to aid in the prevention of dental caries. Dental "caries" is understood as tooth decay, which leads to tooth demineralization. The following amino acids were found to be useful as dental caries preventing agents: glycine, leucine, isoleucine, lysine, methionine, phenylalanine, serine, threonine, valine, tryptophan and mixtures thereof with the following amino acids being sometimes preferred: glycine, phenylalanine, serine, isoleucine, leucine, methionine; with glycine and phenylalanine being sometimes being even more preferred. The amino acids may be natural or synthetic. The amino acids might be in D- or L-configuration. In some embodiments the L-configuration is preferred.

In some embodiments, disclosed compositions can include the amino acids present in the following amounts (wt. % with respect to the weight of the whole composition): at least 0.1, or at least 1, or at least 2 wt. %. In some embodiments, disclosed compositions can include the amino acids present in the following amounts (wt. % with respect to the weight of the whole composition): not more than 15 or not more than 12 or not more than 10 wt. %. In some embodiments, disclosed compositions can include the amino acids present in the following amounts (wt. % with respect to the weight of the whole composition), in a range including and between 0.1 to 15, or a range including and between 1 to 12, or a range including and between 2 to 10 wt. %.

In some embodiments, disclosed compositions include the following concentration of the amino acid, alone or in combination with other amino acids: glycine in an amount of 0.1 to 10 wt. %; or leucine in an amount of 0.1 to 5 wt. %; or isoleucine in an amount of 0.1 to 5 wt. %; or lysine in an amount of 0.1 to 10 wt. %; or methionine in an amount of 0.1 to 10 wt. %; or phenylalanine in an amount of 0.1 to 5 wt. %; or serine in an amount of 0.1 to 10 wt. %; or threonine in an amount of 0.1 to 10 wt. %; or valine in an amount of 0.1 to 8 wt. %; or tryptophan in an amount of 0.1 to 2 wt. %; all of the above in wt. % with respect to the weight of the whole composition.

In some embodiments, disclosed compositions include the following concentration of the amino acid, alone or in combination with other amino acids: glycine in an amount of 1 to 10 wt. %; or leucine in an amount of 1 to 5 wt. %; or isoleucine in an amount of 2 to 5 wt. %; or lysine in an amount of 5 to 10 wt. %; or methionine in an amount of 2 to 10 wt. %; or phenylalanine in an amount of 1 to 5 wt. %; or serine in an amount of 1 to 10 wt. %; or threonine in an amount of 6 to 10 wt. %; or valine in an amount of 3 to 8 wt. %; or tryptophan in an amount of 0.5 to 2 wt. %; all of the above in wt. % with respect to the weight of the whole composition. In contrast, the following amino acids were found to be not effective for caries prevention: proline, arginine, histidine, aspartic acid, glutamine, tyrosine. Some embodiments of the disclosed composition do not contain these amino acids: proline, arginine, histidine, aspartic acid, glutamine, tyrosine. Some embodiments of the disclosed composition contain these amino acids in only in an amount of not more than 0.5 wt. %, or more than 0.3 wt. %, or more than 0.1 wt. % with respect to the weight of the whole composition.

In some embodiments, disclosed compositions do not include any quaternary antimicrobial compounds.

Disclosed compositions can have varied properties. In some embodiments, disclosed compositions can be described by the pH thereof, the viscosity thereof, the stability thereof, various other properties, or combinations thereof.

In some embodiments, disclosed compositions can have a pH that is acceptable for use in the mouth of a person, for example. In some embodiments, disclosed compositions can have a pH from 4.5 to 9.5, for example. In some embodiments, the composition can have a pH in a more neutral range from 5.0-8.5 or 5.5-8.5 for example, as dry mouth sufferers can have a higher sensitivity to pH. The composition can naturally have such a pH or can be buffered to have a pH in a useful, e.g., a "neutral" range.

In some embodiments, disclosed compositions can have a viscosity that renders them useful or deliverable as a sprayable composition. A composition can be sprayable via a non-pressurized dispenser or a pressurized pump dispenser, for example. In some embodiments, disclosed compositions can have a viscosity of not greater than 80,000 centipoise (cps), not greater than 50,000 cps, not greater than 20,000 cps, or not greater than 10,000 cps. In some embodiments, disclosed compositions can have more desirable rheological properties that make them less shear thinning. In some embodiments, less shear thinning compositions have a more widely dispersed spray pattern when delivered in a non-pressurized dispenser.

In some embodiments, disclosed compositions can have desired stability properties. The stability of a composition can include microbiological stability, physical stability, or combinations thereof. In some embodiments, disclosed compositions are microbiologically stable for at least 6 months, in some embodiments 1 year, in some embodiments greater than 2 years.

In some embodiments, disclosed compositions remain physically stable when subjected to normal room temperature conditions, when subjected to temperatures approaching or surpassing the freezing point of the composition and subsequently thawed, or combinations thereof, for example. In some embodiments, the composition can be stable if it does remain physically stable when subjected to normal room temperature conditions, when subjected to temperatures approaching or surpassing the freezing point of the composition and subsequently thawed, or combinations thereof, for example. In some embodiments, disclosed compositions are physically stable when subjected to temperatures above room temperature, for example greater than 60° C. In some embodiments, disclosed compositions are physically stable when subjected to mechanical effects (e.g., gravitational) such as centrifugation, for example. In some embodiments, disclosed compositions are physically stable when subjected to both changes in temperature (such as those discussed above) and mechanical effects (such as those discussed above), for example. In some embodiments, a composition that is physically stable is one that does not separate into oil and water phases over the useful life of the product, during transport and/or storage, or any combinations thereof.

In some embodiments, the sprayable composition that has a low viscosity (<10,000 cps) can be easily remixed to a uniform state by shaking. In some embodiments, disclosed compositions that may be useful as sprayable compositions can have a relatively higher viscosity and are not as easily mixed by shaking. The amount of shaking required to restore a separated emulsion into a state of uniformity is subjective and may be difficult to assess, specifically in opaque packaging. Improper mixing can lead to the dispensing and use of product that is not the intended composition. In some embodiments, disclosed compositions do not separate into oil and water phases when subjected to various conditions and in some embodiments, disclosed compositions do separate into oil and water phases when subjected to various conditions. Compositions that are physically stable may be advantageous because it can provide a uniform composition delivered to the user throughout the life of the product.

In some embodiments, disclosed compositions are physically stable when subjected to at least one freeze/thaw/centrifugation cycle. One freeze/thaw/centrifugation cycle includes freezing the composition (for a minimum of 3 hours for example), subsequently thawing the composition (for a minimum of 2 hours for example) and subsequently centrifuging the composition at 1750 RCF (relative centrifugal force) for 15 minutes. In some embodiments, disclosed compositions are physically stable when subjected to at least two freeze/thaw/centrifugation cycles, or at least three freeze/thaw/centrifugation cycles, for example. In some embodiments, disclosed compositions are physically stable when subjected to temperatures above 60° C., which can be referred to as one heat cycle. In some embodiments, disclosed compositions are physically stable when subjected to at least one heat cycle. In some embodiments, disclosed compositions are physically stable when subjected to at least one freeze/thaw/centrifugation cycle and subsequently one heat cycle.

In some embodiments, disclosed compositions that may be useful as sprayable compositions can have a relatively low viscosity (<10000 cps) for example. In some such compositions, the composition can be useful even if it is not physically stable, as it can be at least temporarily re-suspended into a sprayable composition and sprayed upon shaking (e.g., shaking for 5 seconds to 30 seconds, or 5 seconds to 15 seconds or 5 seconds to 10 seconds). In some embodiments, disclosed compositions can have desired effects when utilized. Such effects can include, for example the composition's effect on biofilms, the composition's effect on plaque buildup, the composition's effect on water loss, the composition's ability to maintain or provide lubricating properties, resist dilution or wash-off by saliva or water, or drinking and eating in general or combinations thereof.

In some embodiments, disclosed compositions can prevent, inhibit, disrupt the formation or maintenance of a biofilm in an area contacted with the composition. The area contacted can be in vivo or in vitro. In some embodiments, a composition can prevent, inhibit, disrupt the formation or maintenance of a biofilm in a mouth of a user where the composition was applied to the mouth, for example via spraying the composition into the mouth when compared to a mouth without the composition applied thereto. In some embodiments, a composition can prevent, inhibit, disrupt the formation or maintenance of a biofilm in a container in which a biofilm exists and the composition was applied to the container via pouring, spraying, etc when compared to a container without the composition applied thereto. Preventing, inhibiting, disrupting, or some combination thereof the formation or maintenance of biofilms can be measured using a modified version of the MBEC assay (described in ASTM E2799), which measures disruption of strep mutans biofilms grown on special pegs in a microtiter plate. The biofilms growing on the pegs are treated by periodic submersion into test materials, followed by washing in saliva and water. The biofilm remaining on each peg following treatment is quantified by measuring the amount of fluorescently labeled bacteria that eluted from the pegs at the end of the treatment cycles (see example). In some embodiments, disclosed compositions can affect the buildup of plaque in an area contacted by the composition. The area contacted can be in vivo or in vitro. In some embodiments, a composition can decrease plaque buildup on at least one tooth in a mouth of a user where the composition was applied to the mouth, for example via spraying the composition into the mouth when compared to a mouth without the composition applied thereto. In some embodiments, a composition can decrease plaque buildup in a container in which plaque can develop and the composition was applied to the container via pouring, spraying, etc. when compared to a container without the composition applied thereto. Decreasing plaque buildup can be measured by a variety of methods in vivo including for example plaque scoring, dyeing of plaque, etc.

In some embodiments, disclosed compositions can affect hydration loss in an area contacted by the composition. The area contacted can be in vivo or in vitro. In some embodiments, a composition can decrease hydration loss in a mouth of a user where the composition was applied to the mouth, for example via spraying the composition into the mouth when compared to a mouth without the composition applied thereto. In some embodiments, a composition can decrease hydration loss from a tissue in which hydration can be lost and the composition was applied to the tissue via pouring, spraying, etc. when compared to a tissue without the composition applied thereto. Hydration loss can be measured by exposing treated tissues of uniform size to a controlled 37° C. environment for a set time period (4 hrs), and recording the % weight loss from the treated tissue sample. The treated tissue is then exposed to high temperature to rid the sample of all water (95° C./4 hrs and 115° C./4 hrs). The water lost at 4 hrs is divided by the total water loss (after the 115° C. step) and is indicative of the water lost from the tissue at 4 hrs. In some embodiments, disclosed compositions can affect less than 65% water loss, or less than 60% water loss.

In some embodiments, disclosed compositions can affect lubricity or lubriciousness of an area contacted by the composition. The area contacted can be in vivo or in vitro. In some embodiments, a composition can maintain or increase lubricity in a mouth of a user where the composition was applied to the mouth, for example via spraying the composition into the mouth when compared to a mouth without the composition applied thereto. In some embodiments, a composition can provide lubricating properties to a mouth to the same degree that saliva can, for example. In some embodiments, a composition can maintain or increase lubricity on a substrate in which lubricity can be lost and the composition was applied to the substrate via pouring, spraying, etc. when compared to a substrate without the composition applied thereto. Lubricity or the ability to provide lubricating properties can be measured by the friction coefficient relative to a suitable substrate. A low friction coefficient (comparable to saliva) is desired.

Disclosed compositions combine the benefits of oil and water phases. In some embodiments, disclosed compositions can combine numerous desired benefits such as lubrication, moisturization, exposure of hard tissue to beneficial minerals, and pH balancing. Finding an ingestible surfactant and thickening system to achieve all of the desired benefits required significant experimental investigation, was non-trivial, and required more than routine optimization. Furthermore, some disclosed compositions also achieve desired physical stability. Emulsions without certain physical stability criteria may have less than desirable product shelf life and commercial usefulness. Stability to freeze/thaw cycles may be important to ensure the emulsion is stable during storage and shipping. It may be commercially less desirable for an emulsion to be separated into water and oil phases before oral application. The unique combination of disclosed surfactants and thickening agents results in emulsion compositions that are physical stable to multiple cycles of freeze/thaw/centrifuge challenge testing and may be resistant to separation when exposed to elevated temperatures (>60 C). Surprisingly some of these formulations also have anti-plaque property as demonstrated by in vitro anti-biofilm studies using *Streptococcus mutans*, a well-known biofilm-forming bacteria responsible for dental plaque.

Also disclosed herein are methods of using disclosed compositions. Disclosed methods can include contacting an oral cavity or oral tissue with a disclosed composition. The step of contacting the oral cavity or oral tissue can be accomplished by applying the composition in any way, for example spraying. Disclosed methods can be useful for preventing, inhibiting, disrupting, or any combination thereof the formation or maintenance of a biofilm in an area contacted with the composition; for affecting hydration loss in an area contacted by the composition; for affecting lubricity or lubriciousness of an area contacted by the composition; for affecting or alleviating the effects of xerostomia, dry mouth, or both.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. For example, a composition that "comprises" silver may be a composition that "consists of" silver or that "consists essentially of" silver.

As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Use of "first," "second," etc. in the description above and the claims that follow is not intended to necessarily indicate that the enumerated number of objects is present. For example, a "second" substrate is merely intended to differentiate from another substrate (such as a "first" substrate). Use of "first," "second," etc. in the description above and the claims that follow is also not necessarily intended to indicate that one comes earlier in time than the other. Example articles and techniques according to the disclosure provide will be illustrated by the following non-limiting examples.

Examples

TABLE 1A

Materials

| Chemical/Material Name | Abbreviation | CAS | Manufacturer |
| --- | --- | --- | --- |
| Water (Deionized) | DI Water | n/a | In house Millipore MilliQ Water System |
| Phosphate Buffer Water 1 | PBW 1 | n/a | see table below |
| Phosphate Buffer Water 2 | PBW 2 | n/a | see table below |
| Dipotassium phosphate | $K_2HPO_4$ | 16788-57-1 | MP Biomedicals; Aurora, OH, USA |
| Monopotassium phosphate | $KH_2PO_4$ | 7778-77-0 | VWR; West Chester, PA, USA |
| Calcium Chloride dihydrate | $CaCl_2*2H_2O$ | 11035-04-8 | Sigma Aldrich; St. Louis, MO, USA |

TABLE 1A-continued

Materials

| Chemical/Material Name | Abbreviation | CAS | Manufacturer |
|---|---|---|---|
| Sodium Chloride | NaCl | 7647-14-5 | EMD OmniPur; Burlington, MA, USA |
| Potassium Chloride | KCl | 7447-40-7 | EMD OmniPur |
| Sodium Hydroxide | NaOH | 1310-73-2 | Ricca Chemical Company |
| Glycerin | Glycerin | 56-81-5 | Spectrum Chemical; New Brunswick, NJ, USA |
| Clinpro ™ Glycine Prophy Powder (>99% glycine) | Glycine | 56-40-6 | 3M Company; St. Paul, MN, USA |
| Xylitol | Xylitol | 87-99-0 | Roquette Pharma; Geneva, IL, USA |
| Erythritol | Erythritol | 149-32-6 | Cargill; Wayzata, MN USA |
| Sorbitol | Sorbitol | 50-70-4 | Sigma Aldrich; St. Louis, MO, USA |
| N-Nonanoyl-N-methylglucamine | MEGA-9 | 85261-19-4 | 3M, St Paul, MN |
| *Aloe Vera* Gel (10X decolorized) | *Aloe Vera* | 85507-69-3 | Terry Laboratories; Melbourne, FL, USA |
| Amylopectin (Naviance Instant Maize) | Amylopectin | 9037-22-3 | National Starch; Monroe, NJ, USA |
| Geogard ECT (Benzyl Alcohol, Salicyclic Acid, Glycerin, Sorbic Acid) | Geogard ECT | 100-51-6 69-72-7 56-81-5 110-44-1 | Lonza Ltd.; South Plainfield, NJ, USA |
| Geogard 221 (Dehydroacetic Acid & Benzyl Alcohol & Water) | Geogard 221 | 100-51-6 520-45-6 | Lonza Ltd.; South Plainfield, NJ, USA |
| Peppermint | Peppermint | 8006-90-4 | Spectrum Chemical; New Brunswick, NJ, USA |
| Medium Chain Triglycerides Oil (NEOBEE M-5) caprylic/capric triglyceride made using glycerol from vegetable oil sources and medium-chain fatty acids from coconut and palm kernel oils | MCT Oil | 73398-61-5 | Stepan; Northfield, IL, USA |
| Hydrogenated Vegetable Oil (Wecobee M) | Hard Veggie Oil | 68334-28-1 | Stepan; Northfield, IL, USA |
| Polyglyceryl-10 Oleate (POLYALDO 10-1-O) | POLYALDO 10-1-O | 9007-48-1 | Lonza Ltd.; South Plainfield, NJ, USA |
| Polyglyceryl-10 Stearate (POLYALDO 10-1-S) | POLYALDO 10-1-S | 79777-30-3 | Lonza Ltd.; South Plainfield, NJ, USA |
| Polyglyceryl-10-Dipalmitate (POLYALDO 10-2-P) | POLYALDO 10-2-P | 67784-82-1 | Lonza Ltd.; South Plainfield, NJ, USA |
| Polyglyceryl-6-Disterate (POLYALDO 6-2-S) | POLYALDO 6-2-S | 34424-97-0 | Lonza Ltd.; South Plainfield, NJ, USA |
| Oleic Acid | Oleic Acid | 112-80-1 | Spectrum Chemical; New Brunswick, NJ, USA |
| Tocopherol Acetate | Vitamin E | 7695-91-2 | Alfa Aesar Tewksbury, MA |
| Oxygenated Glycerol Triesters (Oxidized Corn Oil) | OGT Oil | n/a | Ashland; Covington, KY, USA |
| Cetylpyridinium Chloride | CPC | 6004-24-6 | TCI America; Portland, OR, USA |
| Methylparaben | Methylparaben | 99-76-3 | Spectrum Chemical; New Brunswick, NJ, USA |

TABLE 1B

Materials - Thickeners

| Chemical Name | Abbreviation | CAS | Manf. |
|---|---|---|---|
| *Cyamopsis tetragonoloba* (guar) gum (JAGUAR S) | Natural Guar | 9000-30-0 | Solvay; Belgium |
| Hydroxypropyl Guar (JAGUAR 60-HP) | HP Guar 1 | 39421-75-5 | Solvay; Belgium |
| Hydroxypropyl Guar (JAGUAR HP-8 COS) | HP Guar 2 | 39421-75-5 | Solvay; Belgium |
| Cationic Guar (Hi-Care 1000) | Cationic Guar | 71888-88-5 | Solvay; Belgium |
| Xanthan Gum | Xanthan Gum 1 | 11138-66-2 | Sigma Aldrich |
| Xanthan Gum - High MW (KELTROL Advanced) | Xanthan Gum 2 | 11138-66-2 | CP Kelco; Atlanta, GA, USA |
| Xanthan Gum - Low MW (KELTROL SF) | Xanthan Gum 3 | 11138-66-2 | CP Kelco; Atlanta, GA, USA |
| Carageenan Iota | Carageenan | 9062-07-1 | Sigma Aldrich |
| Polyvinylpyrrolidone K 25 (PLASTIDONE K25) | PVP K 25 | 9003-39-8 616-45-5 | ISP Technologies Inc. Texas City, TX, USA |
| Gellan Gum | Gellan Gum | 71010-52-1 | Alfa Aesar; Tewksbury, MA, USA |
| Gum Arabic | Gum Arabic | 9000-01-51 | Sigma Aldrich |
| Methylcellulose (BENECEL A4M) | MC | 9004-67-5 | Ashland; Covington, KY, USA |
| Hydroxyethylcellulose (Natrosol 250HHX) | HEC | 9004-62-0 | Ashland |
| Hydroxypropylmethyl-cellulose (Benecel K200M) | HPMC 1 | 9004-65-3 | Ashland |
| Hydroxypropylmethyl-cellulose (Methocel K4-M) | HPMC 2 | 9004-65-3 | Amerchol; Edison, NJ, USA |
| Hydroxypropylcellulose (Klucel HF PH) | HPC | 9004-64-2 | Ashland |

TABLE 1B-continued

Materials - Thickeners

| Chemical Name | Abbreviation | CAS | Manf. |
|---|---|---|---|
| Ethylcellulose (Aqualon EC-N7 Pharm) | EC | 9004-57-3 | Ashland |
| Instant Clearjel Food Starch | Food Starch | na | National Starch; Monroe, NJ, USA |
| Amylopectin (Naviance Instant Maize) | Amylopectin | 9037-22-3 | National Starch |
| Polyacrylic Acid (Carbopol 907) | Polyacrylic Acid | 9003-01-4 | Lubrizol; Wickliffe, OH |
| Fumed Silica (Aerosil A300) | Fumed Silica | 112945-52-5 | Evonik; Parsippany, NJ, USA |

TABLE 1C

Commercially available products for treatment of xerostomia

| Product Name | TOOTHETTE Advanced Oral Moisturizer Spray | AQUORAL | LUBRICITY |
|---|---|---|---|
| Manufacturer | Sage Products LLC; Cary, IL, USA | Mission Pharmacal Company; San Antonio, TX, USA | Lubricity Innovations Inc; Buffalo, NY, USA |
| Ingredients | Water, glycerin, xylitol, mint flavor, polysorbate 20, polysorbate 80, potassium sorbate, sodium | 94.4% Oxidized glycerol triesters (OGT), silicon dioxide | water, xylitol, hyaluronan, sodium benzoate, and hyaluronate, cetylpyridinium chloride |

TABLE 1C-continued

Commercially available products for treatment of xerostomia

| | hyaluronate, cetylpyridinium chloride | dioxide, aspartame, and artificial flavoring | potassium sorbate |
|---|---|---|---|
| Delivery Format | mist | jet | mist |
| Viscosity | | | |
| sheer rate = 1/s Pa·s | 0.014 | NT | 0.198 |
| sheer rate = 3.16/s Pa·s | 0.008 | NT | 0.195 |
| sheer rate = 10/s Pa·s | 0.006 | NT | 0.186 |

TABLE 1D

Materials and Composition of Artificial Saliva

| Ingredient | Source | Grams per Liter of Water |
|---|---|---|
| Porcine stomach Mucin type III | Sigma-Aldrich | 2.20 |
| $CaCl_2 \cdot 2H_2O$ | EMD OmniPur | 0.22 |
| KCl | EMD OmniPur | 1.14 |
| NaCl | EMD OmniPur | 0.38 |
| $KH_2PO_4$ | JT Baker | 0.74 |
| Deionized Water | Millipore MilliQ Water System | To 1000 mL |
| 6.0N NaOH | Ricca Chemical Company | To Adjust to pH 7.0 |

Dissolve all components in water. Adjust to pH 7.0. Store refrigerated for up to 1 week. Thoroughly mix before use.

TABLE 2

Phosphate Buffer Water 1 Preparation (pH 7)

| Ingredient per 1 Liter Water | CAS | Source | MW | Grams per Liter | mM | % wt |
|---|---|---|---|---|---|---|
| KCl | 7447-40-7 | VWR; West Chester, PA, USA | 74.55 | 0.63 | 8.38 | 0.0625 |
| $MgCl_2 \cdot 6H_2O$ | 7791-18-6 | VWR; West Chester, PA, USA | 203.30 | 0.06 | 0.29 | 0.0059 |
| $CaCl_2 \cdot 2H_2O$ | 11035-04-8 | Sigma Aldrich | 147.00 | 0.17 | 1.13 | 0.0166 |
| $K_2HPO_4$ | 16788-57-1 | MP Biomedicals; Aurora, OH, USA | 174.18 | 0.80 | 4.62 | 0.0804 |
| $KH_2PO_4$ | 7778-77-0 | VWR; West Chester, PA, USA | 136.09 | 0.33 | 2.40 | 0.0326 |

TABLE 3

Phosphate Buffer Water 2 (w/o Mg/KCl Preparation) pH 7

| Ingredient per 1 Liter Water | CAS | Source | MW | Grams per Liter | mM | % wt |
|---|---|---|---|---|---|---|
| $CaCl_2 \cdot 2H_2O$ | 11035-04-8 | Sigma Aldrich | 147.00 | 0.17 | 1.13 | 0.0166 |
| $K_2HPO_4$ | 16788-57-1 | MP Biomedicals | 174.18 | 0.80 | 4.62 | 0.0804 |
| $KH_2PO_4$ | 7778-77-0 | VWR | 136.09 | 0.33 | 2.40 | 0.0326 |

Example Preparation Procedure

Example formulations were prepared in the following manner. The water phase components were mixed together by dissolving all the water-soluble ingredients and adjusting to a pH of 6-8 (unless otherwise noted) with HCl or NaOH. As required, glycerin and thickener were added to the water phase last, as a slurry, while stirring the solution to prevent clumping. The water phase was heated to 80° C. Next, the oil phase components were mixed together and heated to 80° C. The water phase was then poured into oil phase and the combined mixture was homogenized for 3 minutes at medium speed using a PowerGen 1000 Homogenizer (Fisher Scientific) with a saw-tooth, fine generator probe. Each mixture was rolled and allowed to cool until it reached room temperature; and then allowed to sit motionless for greater than 24 hours prior to further evaluation.

Viscosity Testing

The viscosity of the Example formulations was measured at room temperature on an AR-G2 Magnetic Bearing Rheometer from TA Instruments Ltd., with parallel plate fixture. Approximately 1.4 mL of example formulation was placed between the plates and the gap of the plates was set to 1 mm for the measurement at room temperature. The viscosity was recorded at the shear rate of 1.0, 3.16, and 10 1/s. Two replicates for each formulation were conducted and the average was reported.

Effect of Stabilizing Thickeners on Lubricity (Friction Lowering Effect)

Some stabilizing thickener polymers also provided lubrication, which may impart improved mouth feel or comfort with use during treatment of xerostomia. This property was assessed by friction measurement according to the Friction Test Method, below.

Friction Test Method:

Friction/Lubrication was measured using a FORCEBOARD universal friction tester (Industrial Dynamics, Sweden AB) affixed with a 10 newton (N) load cell. A natural lambskin condom made from sheep cecum (Trojan NATURALAMB™ Luxury Condoms, Church & Dwight Co., Inc. Ewing, N.J.) was used to mimic oral mucosal tissue. The condom was rinsed thoroughly and excess liquid was removed prior to use and between measurements to assure that no residual lubricant or example test formulation interfered with subsequent measurements. The condom was placed on a glass slide, smoothed to remove wrinkles, and clamped to the FORCEBOARD friction tester using a binder clip. A syringe was used to meter 0.5 mL of Example test solution (or other comparative samples such as water, or human saliva) onto the surface of the condom near the front of the FORCEBOARD (farthest from the motor). A second layer of condom was then secured around a gloved finger, and the covered finger was moved down the surface of the FORCEBOARD (toward the motor) while applying a target vertical force of 3 N. This motion was repeated 6-10 times for each replicate measurement. Friction coefficients (at a vertical force of 2.9 to 3.1 N) were calculated by the FORCEBOARD Analyzer software (Industrial Dynamics, Sweden). Unless otherwise noted three replicates for each example were measured and the average friction coefficient was reported in Tables 4A, 4B, 4C, 4E, 4F, and 4J. A low friction coefficient value is more slippery and thus is a desirable property for a formulation to treat xerostomia.

All tested example formulations performed better than water. The addition of polymers such as hydroxypropyl guars (JAGUAR), xanthan gum, or carrageenan (or combinations) may further improve lubrication for emulsions compared to non-polymer containing controls. Addition of more polymer lends to better lubrication properties as well. Higher oil content also improves lubrication properties of example formulations. Among the polymers, hydroxypropyl guar (JAGUAR) polymers provided the most lubrication effect for the example formulations tested.

TABLE 4A

EXAMPLES EX. 1-EX. 6

|  | EX. 1 | EX. 2 | EX. 3 | EX. 4 | EX. 5 | EX. 6 |
|---|---|---|---|---|---|---|
| Water Phase |  |  |  |  |  |  |
| PBW 2 | — | 67.3 | 67.3 | 66.5 | 66.3 | 67.0 |
| Water | 67.4 | — | — | — | — | — |
| Glycerin | 15.0 | 15.0 | 15.0 | 15.0 | 15.0 | 15.0 |
| Xylitol | 5.0 | 5.0 | 5.0 | 5.0 | 5.0 | 5.0 |
| Xanthan Gum 2 | 0.1 | 0.2 | — | — | — | — |
| Xanthan Gum 3 | — | — | 0.2 | — | 0.2 | 0.5 |
| Fumed Silica | — | — | — | 1.0 | 1.0 | — |
| Geogard ECT | 0.5 | 0.5 | 0.5 | 0.5 | 0.5 | 0.5 |
| Peppermint | 2 drops | 2 drops | 2 drops | 2 drops | 2 drops | 2 drops |
| Total % Water Phase: | 88.0 | 88.0 | 88.0 | 88.0 | 88.0 | 88.0 |
| Oil Phase |  |  |  |  |  |  |
| MCT Oil | 9.0 | 8.0 | 8.0 | 8.0 | 8.0 | 8.0 |
| POLYALDO 10-1-S | 1.6 | 1.6 | 1.6 | 1.6 | 1.6 | 1.6 |
| POLYALDO 6-2-S | 0.4 | 0.4 | 0.4 | 0.4 | 0.4 | 0.4 |
| Oleic Acid | 1.0 | 2.0 | 2.0 | 2.0 | 2.0 | 2.0 |
| Total % Oil Phase: | 12.0 | 12.0 | 12.0 | 12.0 | 12.0 | 12.0 |
| Total | 100.0 | 100.0 | 100.0 | 100.0 | 100.0 | 100.0 |
| Viscosity |  |  |  |  |  |  |
| sheer rate = 1/s Pa · s | 2.22 | 3.61 | 2.10 | 0.62 | 6.19 | 5.80 |
| sheer rate = 3.16/s Pa · s | 0.97 | 1.45 | 1.01 | 0.35 | 2.70 | 2.51 |
| sheer rate = 10/s Pa · s | 0.41 | 0.57 | 0.48 | 0.18 | 1.14 | 1.06 |
| Friction Coefficient: | 0.25 | 0.22 | 0.22 | 0.22 | 0.20 | 0.16 |

TABLE 4B

EXAMPLES EX. 7-EX. 10

| | EX. 7 | EX. 8 | EX. 9 | EX. 10 |
|---|---|---|---|---|
| Water Phase | | | | |
| PBW 1 | 56.8 | 57.0 | 46.8 | 47.0 |
| Glycerin | 15.0 | 15.0 | 25.0 | 25.0 |
| Xylitol | 5.0 | 5.0 | 5.0 | 5.0 |
| HP Guar 2 | 0.3 | — | 0.3 | — |
| Geogard ECT | 1.0 | 1.0 | 1.0 | 1.0 |
| Peppermint | 2 drops | 2 drops | 2 drops | 2 drops |
| Total % Water Phase: | 78.0 | 78.0 | 78.0 | 78.0 |
| Oil Phase | | | | |
| MCT Oil | 18.0 | 18.0 | 18.0 | 18.0 |
| POLYALDO 10-1-S | 0.6 | 0.6 | 1.0 | 1.0 |
| POLYALDO 6-2-S | 1.4 | 1.4 | 1.0 | 1.0 |
| Oleic Acid | 2.0 | 2.0 | 2.0 | 2.0 |
| Total % Oil Phase: | 22.0 | 22.0 | 22.0 | 22.0 |
| Total | 100.0 | 100.0 | 100.0 | 100.0 |
| Viscosity | | | | |
| sheer rate = 1/s Pa · s | 7.38 | 2.06 | 2.63 | 1.92 |
| sheer rate = 3.16/s Pa · s | 3.98 | 1.04 | 1.31 | 0.98 |
| sheer rate = 10/s Pa · s | 2.04 | 0.44 | 0.69 | 0.44 |
| Friction Coefficient: | 0.11 | 0.21 | 0.10 | 0.18 |

TABLE 4C

COMPARATIVE EXAMPLE C. EX. 1 and EXAMPLES EX. 11-EX. 15

| | C. EX. 1 | EX. 11 | EX. 12 | EX. 13 | EX. 14 | EX. 15 |
|---|---|---|---|---|---|---|
| Water Phase | | | | | | |
| PBW 1 | 67.0 | 66.5 | 66.5 | 66.5 | 66.5 | 66.5 |
| Glycerin | 15.0 | 15.0 | 15.0 | 15.0 | 15.0 | 15.0 |
| Xylitol | 5.0 | 5.0 | 5.0 | 5.0 | 5.0 | 5.0 |
| Aloe Vera | — | — | — | — | 0.01 | — |
| HP Guar 1 | — | 0.5 | — | — | — | — |
| HP Guar 2 | — | — | 0.5 | — | — | — |
| Natural Guar | — | — | — | 0.5 | — | — |
| PVP K 25 | — | — | — | — | 0.5 | — |
| Xanthan Gum 1 | — | — | — | — | — | 0.5 |
| Geogard 221 | 1.0 | 1.0 | 1.0 | 1.0 | 1.0 | 1.0 |
| Peppermint | 2 drops | 2 drops | 2 drops | 2 drops | 2 drops | 2 drops |
| Total % Water Phase: | 88.0 | 88.5 | 88.0 | 88.0 | 88.0 | 88.0 |
| Oil Phase | | | | | | |
| MCT Oil | 9.0 | 9.0 | 10.0 | 10.0 | 9.0 | 9.0 |
| POLYALDO 10-1-S | 1.6 | 1.6 | 1.6 | 1.6 | 1.6 | 1.6 |
| POLYALDO 6-2-S | 0.4 | 0.4 | 0.4 | 0.4 | 0.4 | 0.4 |
| Oleic Acid | 1.0 | 1.0 | — | — | 1.0 | 1.0 |
| Total % Oil Phase: | 12.0 | 12.0 | 12.0 | 12.0 | 12.0 | 12.0 |
| Total | 100.0 | 100.0 | 100.0 | 100.0 | 100.0 | 100.0 |
| Viscosity | | | | | | |
| sheer rate = 1/s Pa · s | 2.91 | 5.09 | 11.53 | 13.95 | NT | 9.89 |
| sheer rate = 3.16/s Pa · s | 1.28 | 2.91 | 5.13 | 6.28 | NT | 3.92 |
| sheer rate = 10/s Pa · s | 0.58 | 1.50 | 2.16 | 2.65 | NT | 1.54 |
| Friction Coefficient: | 0.28* | NT | 0.10* | 0.09* | NT | 0.19* |

NT = not tested

*n (replicates) for friction testing = 2

TABLE 4D

EXAMPLES EX. 16-EX. 21 (no viscosity testing)

| | EX. 16 | EX. 17 | EX. 18 | EX. 19 | EX. 20 | EX. 21 |
|---|---|---|---|---|---|---|
| Water Phase | | | | | | |
| PBW 1 | 66.5 | 66.5 | 66.5 | 67.0 | 66.5 | 66.5 |
| Glycerin | 15.0 | 15.0 | 15.0 | 15.0 | 15.0 | 15.0 |
| Xylitol | 5.0 | 5.0 | 5.0 | 5.0 | 5.0 | 5.0 |
| Aloe Vera | 0.01 | 0.01 | 0.01 | 0.01 | 0.01 | 0.01 |
| Gum Arabic | 0.5 | — | — | — | — | — |
| HPMC 1 | — | 0.5 | — | — | — | — |
| MC | — | — | 0.5 | — | — | — |
| HEC | — | — | — | — | 0.5 | — |
| HPMC 2 | — | — | — | — | — | 0.5 |
| Geogard 221 | 1.0 | 1.0 | 1.0 | 1.0 | 1.0 | 1.0 |
| Peppermint | 2 drops | 2 drops | 2 drops | 2 drops | 2 drops | 2 drops |
| Total % Water Phase: | 88.0 | 88.0 | 88.0 | 88.0 | 88.0 | 88.0 |
| Oil Phase | | | | | | |
| HPC | — | — | — | 0.5 | — | — |
| MCT Oil | 9.0 | 9.0 | 9.0 | 9.0 | 9.0 | 9.0 |
| POLYALDO 10-1-S | 1.6 | 1.6 | 1.6 | 1.6 | 1.6 | 1.6 |

TABLE 4D-continued

EXAMPLES EX. 16-EX. 21 (no viscosity testing)

|  | EX. 16 | EX. 17 | EX. 18 | EX. 19 | EX. 20 | EX. 21 |
|---|---|---|---|---|---|---|
| POLYALDO 6-2-S | 0.4 | 0.4 | 0.4 | 0.4 | 0.4 | 0.4 |
| Oleic Acid | 1.0 | 1.0 | 1.0 | 1.0 | 1.0 | 1.0 |
| Total % Oil Phase: | 12.0 | 12.0 | 12.0 | 12.0 | 12.0 | 12.0 |
| Total | 100.0 | 100.0 | 100.0 | 99.5 | 100.0 | 100.0 |

TABLE 4E

EXAMPLES EX. 22-EX. 27

|  | EX. 22 | EX. 23 | EX. 24 | EX. 25 | EX. 26 | EX. 27 |
|---|---|---|---|---|---|---|
| Water Phase | | | | | | |
| PBW 1 | 66.5 | 66.5 | 66.5 | 66.5 | 66.5 | 66.5 |
| Glycerin | 15.0 | 15.0 | 15.0 | 15.0 | 15.0 | 15.0 |
| Xylitol | 5.0 | 5.0 | 5.0 | 5.0 | 5.0 | 5.0 |
| *Aloe Vera* | 0.01 | 0.01 | 0.01 | 0.01 | 0.01 | 0.01 |
| Carageenan Iota | — | — | — | 0.5 | — | — |
| Gellan Gum | 0.5 | — | — | — | — | — |
| Food Starch | — | 0.5 | — | — | — | — |
| Amylopectin | — | — | 0.5 | — | — | — |
| Polyacrylic Acid | — | — | — | — | 0.5 | — |
| Cationic Guar | — | — | — | — | — | 0.5 |
| Geogard 221 | 1.0 | 1.0 | 1.0 | 1.0 | 1.0 | 1.0 |
| Peppermint | 2 drops | 2 drops | 2 drops | 2 drops | 2 drops | 2 drops |
| Total % Wate Phaser: | 88.0 | 88.0 | 88.0 | 88.0 | 88.0 | 88.0 |
| Oil Phase | | | | | | |
| MCT Oil | 9.0 | 9.0 | 9.0 | 9.0 | 9.0 | 9.0 |
| POLYALDO 10-1-S | 1.6 | 1.6 | 1.6 | 1.6 | 1.6 | 1.6 |
| POLYALDO 6-2-S | 0.4 | 0.4 | 0.4 | 0.4 | 0.4 | 0.4 |
| Oleic Acid | 1.0 | 1.0 | 1.0 | 1.0 | 1.0 | 1.0 |
| Total % Oil Phase: | 12.0 | 12.0 | 12.0 | 12.0 | 12.0 | 12.0 |
| Total | 100.0 | 100.0 | 100.0 | 100.0 | 100.0 | 100.0 |
| Viscosity | | | | | | |
| sheer rate = 1/s Pa · s | 12.45 | 1.84 | 1.48 | 7.22 | NT | 5.75 |
| sheer rate = 3.16/s Pa · s | 7.09 | 1.00 | 0.81 | 3.44 | NT | 2.40 |
| sheer rate = 10/s Pa · s | 4.23 | 0.52 | 0.44 | 1.54 | NT | 1.05 |
| Friction Coefficient: | NT | NT | NT | 0.18* | NT | NT |

*n (replicates) for friction testing = 2

TABLE 4F

EXAMPLES EX. 28-EX. 35

|  | EX. 28 | EX. 29 | EX. 30 | EX. 31 | EX. 32 | EX. 33 | EX. 34 | EX. 35 |
|---|---|---|---|---|---|---|---|---|
| Water Phase | | | | | | | | |
| PBW 1 | 66.5 | 56.5 | — | — | 66.8 | 66.5 | 67.5 | 67.5 |
| PBW 2 | — | — | 66.5 | 51.3 | — | — | — | — |
| Glycerin | 15.0 | 15.0 | 15.0 | 15.0 | 15.0 | 15.0 | 15.0 | 15.0 |
| Xylitol | 5.0 | 5.0 | 5.0 | 5.0 | 5.0 | 5.0 | 5.0 | 5.0 |
| Sorbitol | — | — | — | 5.0 | — | — | — | — |
| *Aloe Vera* | 0.01 | — | — | — | 0.01 | 0.01 | — | — |
| POLYALDO 10-1-O | — | — | — | 1.0 | — | 1.0 | 1.0 | — |
| MEGA-9 | — | — | 1.3 | — | 1.0 | — | — | 1.0 |
| HP Guar 1 | — | 0.3 | 0.5 | — | 0.5 | 0.5 | 0.5 | 0.5 |
| Xanthan Gum 1 | — | 0.3 | — | — | — | — | — | — |
| Xanthan Gum 3 | — | — | — | 0.2 | — | — | — | — |

TABLE 4F-continued

EXAMPLES EX. 28-EX. 35

|  | EX. 28 | EX. 29 | EX. 30 | EX. 31 | EX. 32 | EX. 33 | EX. 34 | EX. 35 |
|---|---|---|---|---|---|---|---|---|
| Fumed Silica | — | — | — | 1.0 | — | — | — | — |
| Geogard ECT | — | 1.0 | 1.0 | 0.5 | 1.0 | 1.0 | — | — |
| Geogard 221 | 1.0 | — | — | — | — | — | — | — |
| Peppermint | 2 drops | 2 drops | 2 drops | 2 drops | — | — | — | — |
| Total % Water Phase: | 87.5 | 78.0 | 89.3 | 79.0 | 89.3 | 89.0 | 89.0 | 89.0 |
| Oil Phase | | | | | | | | |
| EC | 0.5 | — | — | — | — | — | — | — |
| MCT Oil | 9.0 | 18.0 | — | 20.0 | 9.0 | 9.0 | 9.0 | 9.0 |
| Hard Veggie Oil | — | — | 9.0 | — | — | — | — | — |
| POLYALDO 10-1-S | 1.6 | 1.6 | — | — | — | — | — | — |
| POLYALDO 6-2-S | 0.4 | 0.4 | 0.7 | 1.0 | 0.7 | 1.0 | 1.0 | 1.0 |
| Oleic Acid | 1.0 | 2.0 | 1.0 | — | 1.0 | 1.0 | 1.0 | 1.0 |
| Total % Oil Phase: | 12.5 | 22.0 | 10.7 | 21.0 | 10.7 | 11.0 | 11.0 | 11.0 |
| Total | 100.0 | 100.0 | 100.0 | 100.0 | 100.0 | 100.0 | 100.0 | 100.0 |
| Viscosity | | | | | | | | |
| sheer rate = 1/s Pa · s | 2.30 | 12.69 | 11.14 | 8.58 | 8.72 | 22.58 | NT | NT |
| sheer rate = 3.16/s Pa · s | 1.12 | 5.84 | 5.94 | 3.63 | 4.30 | 8.87 | NT | NT |
| sheer rate = 10/s Pa · s | 0.51 | 2.53 | 2.88 | 1.51 | 2.10 | 3.52 | NT | NT |
| Friction Coefficient: | NT | 0.13 | NT | NT | NT | NT | NT | NT |

TABLE 4G

EXAMPLES EX. 36-EX. 41

|  | EX. 36 | EX. 37 | EX. 38 | EX. 39 | EX. 40 | EX. 41 |
|---|---|---|---|---|---|---|
| Water Phase | | | | | | |
| PBW 2 | 51.5 | 51.5 | 51.5 | 51.5 | 66.5 | 66.5 |
| Glycerin | 15.0 | 15.0 | 15.0 | 15.0 | 10.0 | 10.0 |
| Xylitol | 5.0 | 5.0 | 5.0 | 5.0 | 5.0 | 5.0 |
| Sorbitol | 5.0 | 5.0 | 5.0 | 5.0 | 5.0 | 5.0 |
| Xanthan Gum 3 | 0.5 | 0.5 | 0.5 | 0.5 | 0.5 | 0.5 |
| Geogard ECT | 1.0 | 1.0 | 1.0 | 1.0 | 1.0 | 1.0 |
| Total % Water Phase: | 78.0 | 78.0 | 78.0 | 78.0 | 88.0 | 88.0 |
| Oil Phase | | | | | | |
| EC | — | 0.45 | 0.9 | 0.18 | 0.5 | — |
| MCT Oil | 18.0 | 17.6 | 17.1 | 17.8 | 8.6 | 9.0 |
| POLYALDO 10-1-S | 1.6 | 1.6 | 1.6 | 1.6 | 1.6 | 1.6 |
| POLYALDO 6-2-S | 0.4 | 0.4 | 0.4 | 0.4 | 0.4 | 0.4 |
| Oleic Acid | 2.0 | 2.0 | 2.0 | 2.0 | 1.0 | 1.0 |
| Total % Oil Phase: | 22.0 | 22.0 | 22.0 | 22.0 | 12.0 | 12.0 |
| Total | 100.0 | 100.0 | 100.0 | 100.0 | 100.0 | 100.0 |
| Viscosity | | | | | | |
| sheer rate = 1/s Pa · s | 8.29 | 10.09 | 10.11 | 9.44 | 7.60 | 5.15 |
| sheer rate = 3.16/s Pa · s | 3.42 | 4.14 | 4.06 | 3.89 | 3.22 | 2.20 |
| sheer rate = 10/s Pa · s | 1.38 | 1.70 | 1.64 | 1.59 | 1.31 | 0.94 |

TABLE 4H

EXAMPLES EX. 42-EX. 48

|  | EX. 42 | EX. 43 | EX. 44 | EX. 45 | EX. 46 | EX. 47 | EX. 48 |
|---|---|---|---|---|---|---|---|
| Water Phase | | | | | | | |
| $KH_2PO_4$ | 0.06 | 0.06 | 0.06 | 0.06 | 0.06 | 0.06 | 0.06 |
| $K_2HPO_4$ | 0.16 | 0.16 | 0.16 | 0.16 | 0.16 | 0.16 | 0.16 |

TABLE 4H-continued

EXAMPLES EX. 42-EX. 48

|  | EX. 42 | EX. 43 | EX. 44 | EX. 45 | EX. 46 | EX. 47 | EX. 48 |
|---|---|---|---|---|---|---|---|
| $CaCl_2*2H2O$ | 0.03 | 0.03 | 0.03 | 0.03 | 0.03 | 0.03 | 0.04 |
| Water | 56.2 | 51.2 | 46.2 | 51.2 | 50.2 | 43.0 | 57.6 |
| Glycerin | 15.0 | 15.0 | 15.0 | 20.0 | 15.0 | 20.0 | 20 |
| Xylitol | 5.0 | 5.0 | 5.0 | 5.0 | 5.0 | 10.0 | 5 |
| Erythritol | 10.0 | 10.0 | 10.0 | 5.0 | 10.0 | 13.0 | — |
| Xanthan Gum 3 | 0.5 | 0.5 | 0.5 | 0.5 | 0.5 | 0.5 | 0.5 |
| Sorbitol | — | — | — | — | — | — | 2.5 |
| CPC | 0.05 | 0.05 | 0.05 | 0.05 | 0.05 | 0.05 | 0.05 |
| Total % Water Phase: | 87.0 | 82.0 | 77.0 | 82.0 | 82.0 | 86.8 | 87.0 |
| Oil Phase |  |  |  |  |  |  |  |
| Methylparaben | — | — | — | — | 0.2 | 0.20 | — |
| EC | 0.5 | 0.5 | 0.5 | 0.5 | 0.5 | 0.5 | 0.5 |
| MCT Oil | 10.0 | 15.0 | 20.0 | 15.0 | 15 | 10.0 | 10.0 |
| POLYALDO 10-2-P | 1.8 | 1.6 | 1.6 | 1.6 | 1.6 | 1.6 |  |
| POLYALDO 10-1-S | — | — | — | — | — | — | 1.4 |
| POLYALDO 6-2-S | 0.2 | 0.4 | 0.4 | 0.4 | 0.2 | 0.4 | 0.6 |
| Vitamin E | 0.5 | 0.5 | 0.5 | 0.5 | 0.5 | 0.5 | 0.5 |
| Total % Oil Phase: | 13.0 | 18.0 | 23.0 | 18.0 | 18.0 | 13.2 | 13.0 |
| Total | 100.0 | 100.0 | 100.0 | 100.0 | 100.0 | 100.0 | 100.0 |
| Viscosity |  |  |  |  |  |  |  |
| sheer rate = 1/s Pa · s | 26.69 | 34.24 | 38.4 | 34.82 | 17.67 | 17.1 |  |
| sheer rate = 3.16/s Pa · s | 10.37 | 13.03 | 14.37 | 14.31 | 6.89 | 6.9 |  |
| sheer rate = 10/s Pa · s | 3.78 | 4.69 | 5.1 | 5.15 | 2.57 | 2.9 |  |

TABLE 4I

EXAMPLES EX. 49-EX. 50 with Amino Acid Glycine

|  | EX. 49 | EX. 50 |
|---|---|---|
| Water Phase |  |  |
| KH2PO4 | 0.06 | 0.06 |
| K2HPO4 | 0.16 | 0.16 |
| CaCl2*2H2O | 0.03 | 0.03 |
| Water | 53.7 | 52.7 |
| Glycerin | 15 | 20 |
| Xylitol | 10 | 10 |
| *Aloe Vera* | 1 | — |
| Xanthum Gum 3 (KELTROL SF) | 0.5 | — |
| Glycine (amino acid) | 2 | 4 |
| HP Guar 1 (JAGUAR 60-HP) | — | 0.5 |
| Total % Water Phase: | 82.5 | 87.5 |
| Oil Phase |  |  |
| Methylparaben | 0.20 | 0.20 |
| EC | 0.5 | 0.5 |
| MCT Oil (NEOBEE M-5) | 15.0 | 10.0 |
| POLYALDO 10-2-P | 1.6 | 1.6 |
| POLYALDO 6-2-S | 0.2 | 0.2 |
| Vitamin E (tocopherol acetate) | 0.5 | 0.5 |
| Total % Oil Phase: | 17.50 | 12.50 |
| Total | 100.0 | 100.0 |
| Viscosity |  |  |
| sheer rate = 1/s Pa · s | 12.05 | 17.25 |
| sheer rate = 3.16/s Pa · s | 5.03 | 7.09 |
| sheer rate = 10/s Pa · s | 2.09 | 2.88 |

TABLE 4J

Control Examples and Commercially Available Comparative Examples for Friction Coefficient Testing

| Example: | Water | Human Saliva | TOOTHETTE | AQUORAL | LUBRICITY |
|---|---|---|---|---|---|
| Friction Coefficient: | 0.46 | 0.21 | 0.19 | 0.11 | 0.09 |
| N (replicates) | 7 | 2 | 3 | 3 | 3 |

Stability Testing

Specific polymeric thickeners were added to provide muco-adhesion, lubricity, and substantivity (long-lasting). Some polymeric thickeners provided improved emulsion compatibility and physical stability. Exemplary formulations did not phase separate into oil and water phases after heating to temperatures greater than 60° C. or upon freezing. Physical stability was indicated by no phase separation after centrifugation cycles, which indicated improved potential for long term shelf life. The data shown in Table 5 indicates that room temperature stability does not necessarily guarantee stability to elevated temperature or freeze/thaw/centrifugation conditions. Formulations that pass 3 cycles of freeze/thaw/centrifugation and have a High Temperature Stability of at least greater than 60° C. are preferred.

High Temperature Stability Test Procedure:

Example formulation amounts of 10-20 mL were placed in glass vials and heated, starting at 55° C. Visual observations of phase separation were recorded after a minimum equilibration time of 30 minutes at the target temperature. The temperature was then increased by increments of 5° C. and the formulations were allowed to re-equilibrate for 30 minutes at the new elevated temperature, before visual assessment of phase separation. The temperature was increased up to 90° C. The temperature reported for each example was the temperature at which the formulation showed phase separation. It is preferred that the formulations can sustain stability (not phase separate) at higher temperatures.

Freeze/Thaw/Centrifugation Stability Test Procedure:

Example formulation amounts of 10 mL were placed in 15 mL conical centrifuge tubes. Example formulations were stored at −15° C. for a minimum of 2 hours (typically overnight). Once frozen, formulations were thawed at room temperature for a minimum of 2 hours prior to centrifugation at 1750 RCF for 15 minutes. Phase separation assessments of the formulations were made after each 15-minute cycle of centrifugation at 1750 RCF.

Room Temperature Stability Test Procedure:

Example formulations were stored at room temperature for a minimum of 1 month and then assessed for phase separation. Phase separation indicated instability.

(0.2%) of low MW thickener (Xanthan Gum 3: KELTROL SF) is used. When the low MW Xanthan gum 3 (KELTROL SF) is combined with fumed silica, the formulation EX. 5 is stable to 3 cycles of freeze/thaw/centrifugation. All three of these formulations allow for a mist-type spray delivery from the non-pressurized pump sprayer described. Use of a higher amount (0.5%) of the low molecular weight Xanthan gum 3 also results in a stable formulation EX. 6, but results in a Jet-spray delivery. Comparing EX. 2 and EX. 3, the use of a low level (0.2%) of high molecular weight Xanthan gum 2 (KELTROL Advanced) is more stable to freeze/thaw/centrifugation cycling than use of the low MW Xanthan gum at the same level, but the higher molecular weight polymer results in a Jet-spray delivery. Combinations of the preferred thickeners (at varied molecular weight) and fumed silica can be optimized to provide both stability and more desirable properties for spray application. Comparative examples EX. 40 and EX. 41 similarly show that addition of ethylcellulose to the formulation can yield a formulation with a higher viscosity, yet has a wider (mist-type) spray pattern when dispensed from the same simple, pump spray applicator.

TABLE 6A

Spray-ability for Select Examples

|  | EX. 2 | EX. 3 | EX. 4 | EX. 5 | EX. 6 |
|---|---|---|---|---|---|
| Water Phase |  |  |  |  |  |
| PBW 2 | 67.3 | 67.3 | 66.5 | 66.3 | 67.0 |
| Glycerin | 15.0 | 15.0 | 15.0 | 15.0 | 15.0 |

TABLE 5

Impact of Polymeric Thickener on Formulation Stability

| Example | Thickener used | Viscosity Cps (at 1/s shear rate) | High Temp. Stability | Freeze/Thaw/ Centrifugation Stability | RT Stability after 1 month | RT Stability after additional months |
|---|---|---|---|---|---|---|
| C. EX. 1 (control) | None | 2905 | 75° C. | <1 cycle | Yes | 9 months |
| EX. 11 | HP Guar 1 | 5091 | 90° C. | >3 cycles | Yes | 9 months |
| EX. 13 | Natural Guar | NT | 90° C. | >3 cycles | Yes | 8 months |
| EX. 14 | PVP K25 | NT | 65° C. | <1 cycle | No | n/a |
| EX. 15 | Xan. Gum 1 | 9892 | 90° C. | >3 cycles | Yes | 8 months |
| EX. 16 | Gum Arabic | NT | 65° C. | <1 cycle | No | n/a |
| EX. 17 | HPMC 1 | NT | 60° C. | <1 cycle | No | n/a |
| EX. 18 | MC | NT | 65° C. | <1 cycle | No | n/a |
| EX. 19 | HPC | NT | 70° C. | <1 cycle | No | n/a |
| EX. 20 | HEC | NT | 65° C. | <1 cycle | No | n/a |
| EX. 21 | HPMC 2 | NT | 60° C. | <1 cycle | No | n/a |
| EX. 22 | Gellan Gum | 12450 | 85° C. | <1 cycle | Yes | n/a |
| EX. 23 | Food Starch | 1838 | 70° C. | <1 cycle | Yes | n/a |
| EX. 24 | Amylopectin | 1478 | 65° C. | <1 cycle | Yes | 8 months |
| EX. 25 | Carageenan | 7222 | 55° C. | >3 cycles | Yes | n/a |
| EX. 26 | Polyacrylic Acid | NT | 55° C. | <1 cycle | Yes | 8 months |
| EX. 27 | Cationic Guar | 5750 | 60° C. | <1 cycle | Yes | 8 months |
| EX. 28 | EC | 2302 | 85° C. | <2 cycles | No | n/a |

Food grade fumed silica (Evonik A300) is useful for modulating the rheology to achieve a mist-type spray alone or in combination with the mentioned stabilizing thickeners. When used at higher levels, it enhances the stability of the emulsion as demonstrated by freeze/thaw/centrifugation cycling and is heat resistant (high melt temp). Refer to Table 6A. At a use level of 1%, the formulation EX. 4 is more resistant to Freeze/thaw/centrifugation cycling compared to a similar formulation such as EX. 3, but where a low level TABLE 6A-continued Spray-ability for Select Examples

|  | EX. 2 | EX. 3 | EX. 4 | EX. 5 | EX. 6 |
|---|---|---|---|---|---|
| Xylitol | 5.0 | 5.0 | 5.0 | 5.0 | 5.0 |
| Xanthan Gum 2 | 0.2 | — | — | — | — |

TABLE 6A-continued

Spray-ability for Select Examples

|  | EX. 2 | EX. 3 | EX. 4 | EX. 5 | EX. 6 |
|---|---|---|---|---|---|
| Xanthan Gum 3 | — | 0.2 | — | 0.2 | 0.5 |
| Fumed Silica | — | — | 1.0 | 1.0 | — |
| Geogard ECT | 0.5 | 0.5 | 0.5 | 0.5 | 0.5 |
| Peppermint | 2 drops | 2 drops | 2 drops | 2 drops | 2 drops |
| Total % Water: | 88.0 | 88.0 | 88.0 | 88.0 | 88.0 |
| Oil Phase |  |  |  |  |  |
| MCT Oil | 8.0 | 8.0 | 8.0 | 8.0 | 8.0 |
| POLYALDO 10-1-S | 1.6 | 1.6 | 1.6 | 1.6 | 1.6 |
| POLYALDO 6-2-S | 0.4 | 0.4 | 0.4 | 0.4 | 0.4 |
| Oleic Acid | 2.0 | 2.0 | 2.0 | 2.0 | 2.0 |
| Total % Oil: | 12.0 | 12.0 | 12.0 | 12.0 | 12.0 |
| Total | 100.0 | 100.0 | 100.0 | 100.0 | 100.0 |
| High Temp. Stability in ° C. | 85 | 80 | 85 | 90 | 90 |
| Viscosity @ sheer rate = 1/s Pa · s | 3.61 | 2.10 | 0.62 | 6.19 | 5.80 |
| Freeze/Thaw/Centrif. Stab. cycles | <2 | <1 | <2 | <3 | <3 |
| Misting Spray-ability | NO | YES | YES | YES | NO |

TABLE 6B

Spray-ability for Select Examples

|  | EX. 30 | EX. 31 | EX. 40 | EX. 41 |
|---|---|---|---|---|
| Water Phase |  |  |  |  |
| PBW 2 | 66.5 | 51.3 | 66.5 | 66.5 |
| Glycerin | 15.0 | 15.0 | 10.0 | 10.0 |
| Xylitol | 5.0 | 5.0 | 5.0 | 5.0 |
| Sorbitol | — | 5.0 | 5.0 | 5.0 |
| POLYALDO 10-1-O | — | 1.0 | — | — |
| MEGA-9 | 1.3 | — | — | — |
| HP Guar 1 | 0.5 | — | — | — |
| Xanthan Gum 3 | — | 0.2 | 0.5 | 0.5 |
| Fumed Silica | — | 1.0 | — | — |
| Geogard ECT | 1.0 | 0.5 | 1.0 | 1.0 |
| Peppermint | 2 drops | 2 drops | — | — |
| Total % Water: | 89.3 | 79.0 | 88.0 | 88.0 |
| Oil Phase |  |  |  |  |
| EC | — | — | 0.5 | — |
| MCT Oil | — | 20.0 | 8.6 | 9.0 |
| Hard Veggie Oil | 9.0 | — | — | — |
| POLYALDO 10-1-S | — | — | 1.6 | 1.6 |
| POLYALDO 6-2-S | 0.7 | 1.0 | 0.4 | 0.4 |
| Oleic Acid | 1.0 | — | 1.0 | 1.0 |
| Total % Oil: | 10.7 | 21.0 | 12.0 | 12.0 |
| Total | 100.0 | 100.0 | 100.0 | 100.0 |
| High Temp. Stability in ° C. | 60 | 80 | 90 | 90 |
| Viscosity @ sheer rate = 1/s Pa · s | 11.14 | 8.58 | 7.60 | 5.15 |
| Freeze/Thaw/Centrif. Stab. cycles | <3 | <3 | <3 | <3 |
| Misting Spray-ability | NO | NO | YES | NO |

In-Vitro Hydration Retention Test Method (Thermogravimetric Analysis)

A LECO Thermogravimetric Analyzer (TGA) was used to determine the percentage weight loss of samples to simulate 4-hour moisture retention in the oral cavity. In this in-vitro test, sliced, raw beef roast approximately 6 mm thick was used to mimic soft tissue. A circular biopsy punch 1 cm diameter was taken from the raw roast beef slice to create disc-shaped tissue section samples. These samples were pre-weighed and then coated by immersing the tissue samples in one of the commercially available xerostomia alleviation products, example formulations, or raw materials (oil only). An uncoated beef sample was also analyzed as a control. Approximately 0.2 g of test material was weighed into a foil liner analysis container and placed into the LECO TGA Thermogravimetric Analyzer. The examples were then held at body temperature (37° C.) for 4 hours, and the percent (%) volatiles (water) lost after this step was recorded. Next, the temperature was increased to burn off all volatile materials and obtain the total weight fraction. The weight of lost after the 37° C. at the 4-hour step point was divided by the total volatiles, and expressed as a percentage (%) of total volatiles lost at 4 hours. The following table shows the details of the time/temperature profile used to run the program on the LECO TGA Thermogravimetric Analyzer.

TABLE 7

LECO TGA Program

| PARAMETER | Step 1 | Step 2 | Step 3 |
|---|---|---|---|
| Covers | No | No | No |
| Start Temp. ° C. | 25 | 37 | 95 |
| End Temp. ° C. | 37 | 95 | 115 |
| Ramp Rate | 1 | 5 | 1 |
| Ramp Time: hours:min | 00:12 | 00:11 | 00:20 |
| Hold Time: hours:min | 04:00 | 04:00 | 04:00 |
| Total Time: hours:min | 04:12 | 04:11 | 04:20 |
| Max Time: hours:min | 04:20 | 04:20 | 04:20 |
| Atmosphere | Air | Air | Air |
| Flow Rate | Medium | Med High | Med High |
| Window | 3 | 3 | 3 |

In-Vitro Hydration Retention Test Results Summary

Data for commercially available products and example formulations, as well as selected raw materials are summarized in the Table 8 below. All commercial spray products that are water-based averaged water loss at 4 hours at 37° C. of greater than 65%. Most example formulations showed superior performance with less than 65% water loss after 4 hours at 37° C. Most desirable formulations have a water loss of less than 60%.

TABLE 8

In-Vitro Hydration Retention Test Results

| Example/Test Material | N | Average % Total volatiles lost at 4 hours @ 37° C. | Minimum % volatiles lost | Maximum % volatiles lost |
|---|---|---|---|---|
| Control - uncoated | 42 | 80.9 | 67.3 | 92.7 |
| AQUORAL | 24 | 43.4 | 23.6 | 73.6 |
| LUBRICITY | 3 | 70.0 | 68.5 | 70.9 |
| 100% Olive oil | 9 | 67.9 | 41.6 | 89.3 |
| 100% OGT oil | 3 | 68.9 | 63.8 | 75.2 |
| 100% MCT oil | 3 | 69.8 | 68.6 | 71.8 |
| 95% Olive oil + 5% A300 fumed silica | 3 | 44.4 | 39.9 | 49.5 |
| C. EX. 1 | 3 | 51.6 | 46.2 | 60.5 |
| EX. 1 | 3 | 56.1 | 54.7 | 57.9 |
| EX. 25 | 3 | 56.8 | 51.1 | 62.8 |
| EX. 33 | 3 | 61.0 | 58.8 | 64.0 |
| EX. 29 | 3 | 61.3 | 56.5 | 63.8 |
| EX. 5 | 3 | 62.1 | 57.4 | 67.6 |
| EX. 30 | 6 | 66.3 | 57.1 | 73.2 |
| EX. 42 | 3 | 51.6 | 44.3 | 58.7 |
| EX. 43 | 3 | 52.4 | 49.6 | 51.9 |
| EX. 44 | 3 | 51.5 | 49.5 | 53.0 |
| EX. 45 | 3 | 55.3 | 50.4 | 53.0 |

Short Term Wash-Off Resistance Test Method

The following test method was used to simulate wash-off of example formulations from human oral surfaces. A test substrate was created; by using clear, rectangular LEXAN resin polycarbonate test coupons (13 cm×5 cm, 0.74 mm thickness; available from AeroMat Plastics, of Burnsville, Minn., USA). This material was used as a test substrate because it has surface properties similar to human skin. The coupons were prepared by creating a grid of 1 cm×1 cm squares on the back side (non-coated side) to aid in end-point visualization. Examples EX. 36, EX. 37, EX. 38, and EX. 39 were dyed by adding 2 drops of blue food coloring (McCormick Food Color and Egg Dye) to 20 mL of each example formulation. A pull-down knife coater with a gap setting of 0.5 mm was used to coat the surface of the test coupon with example formulations. A foam swab was then used to remove excess material and create precise 2 cm×2 cm square coatings of example formulation aligned over the grid. The coupon was held vertically along the upper long-edge of the coupon and repeatedly submerged in a large water bath at room temperature (22 C+/−2 C). Each downward motion resulted in complete submersion of the coupon. Each upward motion completely removed the coupon from the water bath. Each downward or upward motion was performed continuously over the course of 1 second, so that one complete submersion/removal cycle lasted approximately 2 seconds. Wash-off resistance of each example formulation was determined by counting the number of submersions required to remove at least 75% of the coating from the original coated 2 cm×2 cm area. Four replicates were performed for each example formulation and the results data are shown in Table 9. The results demonstrate that increasing concentrations of ethyl cellulose required more submersions to wash off the coupon (increasing wash-off resistance) and thus should have improved retention in the oral cavity.

TABLE 9

Short Term Wash-off Resistance Test Results

| Example | EX. 36 | EX. 37 | EX. 38 | EX. 39 |
|---|---|---|---|---|
| % EC content | 0 | 0.45 | 0.9 | 0.18 |
| Average number of submersion cycles to wash off >75% | 19.0 | 43.8 | 52.3 | 28.8 |
| Std. Dev. | 4.2 | 5.7 | 5.7 | 6.1 |

Long Term Wash-Off Resistance Test Method (with Artificial Saliva)

The following test method was used to demonstrate the long-term substantive presence (substantivity) of coatings of various compositions when soaked in a large volume of artificial saliva. A glass microscope slide (VWR part #48312-002) is weighed or tared before application of a small amount (approximately 0.2 grams) of sample material to the end of the glass slide away from the rough end used for labeling and holding the slide. The material is then coated evenly by spreading the material over a 1 in.×1 in. (2.5 cm×2.5 cm) area at the edge of the slide using a gloved finger. The amount of material coated on the slide is then quantified by weighing the coated slide. The applied amount of material should be 0.04 gram+/−0.005 gram The coated edge of the slide is then fully immersed in a sufficient volume (50 mL) of artificial saliva (composition in Table 1D) and allowed to sit undisturbed in the vertical position. The slide is removed from the artificial saliva at 30 minutes, 1 hour, and 2 hours. Visual observations of the presence/absence of the coated sample are recorded at those time points.

TABLE 10

Long Term Wash-off Resistance Test Results

| Sample | Coated weight | Observation at 5 min | Observation at 30 min | Observation at 1 hr | Observation at 2 hr |
|---|---|---|---|---|---|
| BIOTENE Spray | 0.042 | Product is only coating about 60% of the slide. | Product has essentially been removed from the slide after 30 min exposure to the artificial saliva. | No change from 30 minutes. | No change from 1 hour. |
| AQUORAL | 0.044 | Yellowish oily residue covering the 2.5 cm² square where product was applied. | Yellowish oily residue covering about 75% of the 2.5 cm² square. Product is starting to pool into larger drops. | No change from 30 minutes. | No change from 1 hour. |
| EX. 46 | 0.044 | Whitish residue covering the 2.5 cm² square where product was applied. | Whitish residue covering about 80% of the 2.5 cm² square. Product is retaining its coated form. | Whitish residue covering about 75% of the 2.5 cm² square. Product is starting to run to the base of the slide. | Residue still covering about 50% of the square. |

Biofilm Disruption Test Method

This method utilizes the high throughput MBEC assay system (Innovotech, Calgary, AB Canada). The method evaluates efficacy of a treatment in disrupting biofilm by quantifying the amount of fluorescent-labeled biofilm remaining on MBEC inoculator pegs after exposure to relevant treatment conditions. The assay is similar to ASTM E2799-12 (Standard Method for Testing Disinfectant Efficacy against *Pseudomonas aeruginosa* Biofilm using the MBEC™ Assay) but was modified for use with *Streptococcus mutans* as the relevant organism and used a modified protocol for exposure of the biofilms to test materials.

MBEC Assay Procedure:

An overnight culture of *Streptococcus mutans* (ATCC 25175) was prepared by using a sterile inoculation loop to introduce a small amount of frozen stock into 5 mL of BHI broth in a 15-mL conical tube. The tube was grown at 37° C. (static, not shaking) for 12-16 hours. The density of the overnight culture is estimated by turbidity measurement (OD600), and diluted appropriately to OD600=0.01 in BHI media supplemented with 1% Sucrose and 1 uM Alexa Fluor® 488 dextran—10,000 MW (Molecular Probes® PN/D22910) to obtain an appropriate volume of inoculum to fill the required 96-well plate. 150 uL of inoculum is added to the appropriate wells of a 96 well MBEC™ Biofilm Inoculator plate (Innovotech® P&G Panel, polystyrene). Control wells for fluorescence readings were also filled with 150 uL of PBS or non-bacteria containing BHI+1% sucrose media. The MBEC inoculator lid (with pegs positioned to be submerged in each well) is placed over the inoculated plate. The plate is wrapped in parafilm and incubated in a sealed plastic container humidified by lining the bottom of the plastic container with a wet paper towel (37° C., shaking at 250 RPM). A biofilm was allowed to form on the pegs for 4 hours prior to exposure of the biofilms to example formulation. In this modified assay, the biofilms growing on the pegs were exposed the example formulations 3 times during the assay, at 4, 7 and 24 hours post inoculum. The exposure to example formulations was performed as a treatment cycle with additional washing steps in saliva and water. Treatment occurred by transferring the pegs into various 96-well plates filled with 150 uL/well of example formulations or 150 uL/well of artificial saliva or water.

Treatment cycle steps (performed at 4, 7, and 24 hours)
1) 2-minute exposure to test materials (150 uL/well)—RT—no shaking)
2) 7-Minute exposure to artificial saliva (150 uL/well) 37° C., shaking)
3) 10-minute exposure to sterile water (150/well) 37° C., shaking)

After the water rinse, the pegs were returned to a 96 well plate filled with growth media (BHI+1% Sucrose+1 uM Alexa Fluor® 488 dextran-10,000 MW) and returned to the incubator to allow for additional biofilm accumulation until the next treatment or until the end of the final growth period. Following the last treatment exposure cycle (at 24 hours post inoculation), the pegs were incubated in growth media for an additional 4 hours before transferring the MBEC pegs into a final wash plate for 1 minute (containing 150 uL sterile water per well, shaking at 37° C. for final rinsing), and then into a 96 well plate (Black plate, suitable for fluorescence quantification in a plate reader) filled with 150 uL/well 50 U/mL dextranase (from *Penicillum* sp., Sigma® D4668-1KU) in 0.2M Acetate, pH 5.5. The pegs were incubated in the extraction solution wells by shaking at 250 RPM at 37° C. for 30 minutes. The plate was then placed in a sonicating water bath for at least 1 hour at room temperature to elute the accumulated biofilm from the pegs into the Dextranase/Acetate solution. Following sonication, the fluorescence in each well is read in a fluorescence plate reader (excitation=488 nm, emission=525 nm). Replicates of 4-8 wells per treatment were performed.

Biofilm Disruption Test Method Results

Table 11 shows the average relative fluorescence reading for each example formulation treatment. A low value shows more biofilm disruption activity than a high value. Values are reported as relative fluorescence (%) normalized to the average fluorescence value for wells containing sterile water as treatment negative control. For consistency, each MBEC plate was run with appropriate replication of sterile water treatment wells. Data are normalized with water controls run in the same 96 well plate. A p-value I provided for each sample compared to water calculated using the students T-test (1-tailed, unpaired).

PERIDEX mouth rinse (0.12 wt-% chlorhexidine gluconate, 3M Health Care, St. Paul, Minn.) was used as a positive treatment control and is expected to show no biofilm accumulation. BIOTENE Dry Mouth Oral Rinse was used as a commercially available product, comparative example, used for treatment of xerostomia (available from GlaxoSmithKiine Consumer Healthcare L.P., Moon Township; PA, USA; ingredients include: purified water, propylene glycol, xylitol, hydrogenated starch hydrolysate, Poloxamer 407, hydroxyethylcellulose, sodium benzoate, Flavor (Peppermint oil), benzoic acid, disodium phosphate, zinc gluconate, lactoferrin, lysozyme, lactoperoxidase; potassium thiocyanate, aloe vera gel, calcium lactate, glucose oxidase).

TABLE 11

Biofilm Disruption Test Results

| Control/ Example | Plate/ Experiment | Replicate wells (N) | Average Absolute Fluorescence | Normalized Relative Fluorescence (%) | P-value (different from water) |
| --- | --- | --- | --- | --- | --- |
| Water | 1 | 8 | 14356 | 100 | n/a |
| PERIDEX | 1 | 8 | 464 | 3 | 0.04 |
| BIOTENE Rinse | 1 | 8 | 38582 | 269 | 0.02 |
| EX. 33 | 1 | 8 | 851 | 6 | 0.05 |
| C. EX. 1 | 1 | 8 | 900 | 6 | 0.14 |
| EX. 32 | 1 | 8 | 971 | 7 | 0.05 |
| EX. 30 | 1 | 8 | 486 | 3 | 0.04 |
| Water | 2 | 4 | 28903 | 100.0 | n/a |
| PERIDEX | 2 | 4 | 1033 | 3.6 | 0.1 |
| BIOTENE Rinse | 2 | 4 | 16416 | 56.8 | 0.19 |
| EX. 34 | 2 | 4 | 1400 | 4.8 | 0.08 |
| EX. 35 | 2 | 4 | 1038 | 3.6 | 0.08 |

Bovine Tooth Hardness Measurement Method
Enamel Chip Preparation and Polish Procedure:

Bovine incisors enamel were cut approximately 4.5 mm×4.5 mm chips and potted in a 1-inch (2.54 cm) diameter cast ring mold with acrylic resin. The enamel chip was faced up. The potted enamel chip was sanded down with 120 grit sandpaper to expose the enamel chip. The enamel side was wet grinded with 600 grit sandpaper (counter-clockwise rotation, 150 rpm, 10 pounds pressure) for 30 seconds. Reversed the direction on the wheel and repeated polishing for another 30 seconds. Reversed direction on the wheel again and repeated polishing for another 30 seconds. Examined the specimens to ensure samples have been sanded down fully (all corners have been exposed) before moving on to the polishing step.

For the polishing step the sandpaper plate was removed and replaced it with the 9-micron polishing plate and added a couple drops of polishing fluid to the plate. Polishing time was set for four minutes, at 130 rpm, clockwise rotation with 10 pounds of pressure. Polished the samples and cleaned them with cotton swabs soaked in a 1:3 mixture of MUR- PHY OIL SOAP (available from Colgate Palmolive Company of New York, N.Y., USA) in DI water, then thoroughly rinsed the samples with DI water. Examined the samples to verify they were adequately polished (a flawed sheen with no visible unpolished areas). If samples were not fully polished, repeated this polishing step as needed. The next step was to remove the 9-micron polishing plate and replace with the 3-micron polishing plate and add a couple drops of polishing fluid to the plate. Polishing time was set for four minutes, at 130 rpm, counter-clockwise rotation with 10 pounds of pressure. Polished the samples and cleaned them with cotton swabs soaked in a 1:3 mixture of MURPHY OIL SOAP in DI water, then thoroughly rinsed the samples with DI water. Examined the samples to verify they were adequately polished (a flawed sheen with no visible unpolished areas). If samples were not fully polished, repeated this polishing step as needed. The next step was to remove the 3-micron polishing plate and replace with the master polishing plate and added a couple drops of 0.02 micron polishing fluid to the plate along with ~50 mL of DI water. Polishing time was set for two minutes, at 120 rpm, counter-clockwise rotation with 8 pounds of pressure. Polished the samples and cleaned them with cotton swabs soaked in a 1:3 mixture of MURPHY OIL SOAP in DI water, then thoroughly rinsed the samples with DI water. Samples were examined. If the samples were adequately polished, they exhibited a near flawless shine and the polishing process was complete. If samples were not fully polished this polishing step was repeated as needed.

Polished Enamel Chip Demineralization Procedure:

A demineralization solution was prepared in the following manner. First an "aged" DL-lactic acid solution was prepared by letting the 0.1M DL-lactic acid solution sit for at least 50 days at room temperature before use, or for seven hours in a steam bath, at approximately 90° C. This is necessary to hydrolyze the lactate polymers to monomers. Next an amount of 500 mL of saturated HAP (hydroxyapatite)/in 0.1 M aged DL-lactic acid solution was placed into a 1000 mL beaker with stirring with a magnetic stir bar. An amount of 200 mL of 1% CARBOPOL 907 solution was added to the beaker. An amount of 50 mL of 0.1 M aged DL-lactic acid solution was added to the beaker. An amount of 200 mL of DI water was added to the beaker. The pH was adjusted to 5.0 with 6N NaOH and the total volume was brought to 1000 mL with additional DI water. The pH was adjusted if necessary. The final demineralization solution contained: 0.1 M DL-lactic acid, 0.2% CARBOPOL 907, 50% saturated with respect to hydroxyapatite and final pH 5.0. Placed 30 mL of demineralization solution into a 50-mL centrifugal tube and screwed the cap on. Placed the tube into a processing oven set to 37° C. for at least four hours or until the solution reached a temperature of 37° C. Placed the polished bovine sample into the centrifugal tube so that the whole sample was immersed into the demineralization solution. The sample was kept immersed in the solution for twenty-four hours at 37° C. Any bubbles that were observed on the surface of the sample were removed (dislodged) by tapping the side of the tube. The samples were checked periodically, and the tube was tapped to dislodge any bubbles that were observed on the enamel surface. After twenty-four hours in the solution, the samples were removed from the solution and rinsed three times with approximately 150 mL of deionized water. Excess water on the surface of the enamel was wiped away with Kim Wipes Delicate Task Wipes paper towel. Samples were stored in a moist environment in the refrigerator until ready to use.

Samples were treated with different liquid materials for the demineralized of the enamel chips samples. All treatments were run in triplicate.

Treatment Group 1 (DI water—Negative Control): One mL of DI water was transferred into a small speed mix cup. The potted tooth sample was placed in the cup, and 1 mL of DI water was transferred onto the sample (ensuring the entirety of the bovine chip surface was covered). The replicate cups were capped and incubated in a 37° C. oven for 24 hours. At 24 hours, the samples were removed, and hardness measurements were taken.

Treatment Group 2 (Artificial saliva—Positive Control): One mL of artificial saliva (Composition in Table 1D) was transferred into a small speed mix cup. The potted tooth sample was placed in the cup, and 1 mL of artificial saliva was transferred onto the sample (ensuring the entirety of the bovine chip surface was covered). The replicate cups were capped and incubated in a 37° C. oven for 24 hours. At 24 hours, the samples were removed, and hardness measurements were taken.

Treatment Group 3 (Example 48): One mL of artificial saliva was transferred into a small speed mix cup. The potted tooth sample was placed in the cup, and 1 mL of EX. 48 was transferred onto the sample (ensuring the entirety of the bovine chip surface was covered). The replicate cups were capped and incubated in a 37° C. oven for 4 hours. After four hours, the samples were removed from the container, and rinsed thoroughly with DI water. One mL of artificial saliva was transferred into each small speed mix cup and the potted tooth sample was placed in the cup and covered with 1 mL of EX. 48. The replicate cups were capped and placed into the 37° C. oven for 2 hours. After two hours, the samples were removed from the container, and rinsed thoroughly with DI water. One mL of artificial saliva was transferred into a small speed mix cup and the potted tooth samples were again placed in the cup and covered with 1 mL of EX. 48. Replicate cups were capped and placed in the 37° C. oven for an additional 18 hours before being removed and rinsed thoroughly with DI water. At 24 hours, the samples were removed, and hardness measurements were taken. The rinsing was done to simulate drinking throughout a day.

Hardness Measurement

The hardness of each sample was measure on Buehler 5104 microhardness machine with setting of these parameters, 200 gf (1.96 newtons), 15 seconds dwell time, Vickers indenter, 20× optical power. The hardness of each chip was measured at 4 points at different corners after demineralization and remineralization. Ten (10) enamel chips were used for every inventive and comparative samples. The average hardness was reported in units of Vickers microhardness (VHN)

TABLE 12

Microhardness Results

| Treatment | Baseline (Demineralization) Average | Post Treatment (Remineralization) Average | Baseline Stdev | Treatment Stdev |
|---|---|---|---|---|
| DI Water (Negative Control) | 38.80 | 38.64 | 9.49 | 9.18 |
| Artificial Saliva (Positive Control) | 39.27 | 46.36 | 9.76 | 9.20 |
| EX. 48 | 40.29 | 47.04 | 9.79 | 12.40 |

ILLUSTRATIVE EMBODIMENTS

1. A composition comprising:
from 5 wt-% to 30 wt-% of one or more plant based oils based on the total weight of the composition;
from 70 wt-% to 95 wt-% of an aqueous phase based on the total weight of the composition;
from 0.1 wt-% to 5 wt-% total of one or more surfactants, based on the total weight of the composition, wherein the one or more surfactants are selected from the group consisting of (i) ethylene oxide/propylene oxide (EO/PO) free, nonionic surfactants, (ii) a surfactant of formula I:

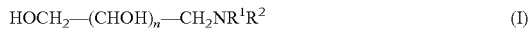

$$HOCH_2-(CHOH)_n-CH_2NR^1R^2 \quad (I)$$

wherein $R^1$ and $R^2$ are independently selected from the group consisting of a hydrogen atom, an alkyl group, $C(O)R^3$, and $SO_2R^4$; with W and $R^4$ being independently selected from the group consisting of an alkyl group, an aryl group, and an aralkyl group; wherein n is an integer from about 2 to about 5; and (iii) combinations of surfactants from surfactant group (i) and surfactant group (ii);
from 0.05 wt % to 3 wt-% total of one or more viscosity modifiers, based on the total weight of the composition, wherein the viscosity modifier is selected from the group consisting of (i) an edible polymeric viscosity modifier, (ii) a silica containing viscosity modifier; and (iii) combinations of viscosity modifier group (i) and viscosity modifier group (ii);
wherein the composition has a pH from 4.5 to 9.5, the composition is an oil in water (o/w) emulsion, and the composition is edible.
2. The composition according to clause 1, wherein the viscosity modifier comprises fumed silica present in an amount not less than 0.5 wt-%. based on the total weight of the composition.
3. The composition according to clause 1, wherein the one or more ethylene oxide/propylene oxide (EO/PO) free, nonionic surfactants is a polyglycerol ester surfactant.
4. The composition according to clause 1, wherein the surfactant comprises the surfactant of formula I, and wherein the viscosity modifier is present in an amount not greater than 2-wt % based on the total weight of the composition.
5. The composition according to clause 1, wherein the aqueous phase is from 75 wt-% to 90 wt-% based on the total weight of the composition.
6. The composition according to clause 1, wherein the one or more edible plant based oils are selected from: sunflower oil, safflower oil, olive oil, coconut oil, palm oil, peanut oil, soybean oil, linseed oil, rapeseed oil, flaxseed oil, hempseed oil, cocoa butter, walnut oil, corn oil, grape seed oil, sesame oil, groundnut oil, wheat germ oil, cottonseed oil, fish oil, watermelon seed oil, lemon oil, orange oil, thistle oil, tomato seed oil, almond oil, *perilla* oil, canola oil, pistachio oil, hazelnut oil, and avocado oil.
7. The composition according to clause 1, wherein the one or more edible plant based oils are from 10 wt-% to 25 wt-% based on the total weight of the composition.
8. The composition according to clause 7, wherein the one or more edible plant based oils are from 15 wt-% to 22 wt-% based on the total weight of the composition.
9. The composition according to clause 1, wherein the composition comprises ethylcellulose as a viscosity modifying agent.
10. The composition according to any of clauses 1 to 9 further comprising at least one of the following: sweeteners, humectants, mineral salts, remineralizing agents, caries preventing agents, buffering components, flavorants, preservative agents, or combinations thereof
11. The composition according to any of clauses 1 to 9 further comprising at least one of the following: aloe vera, folic acid, hyaluronic acid, ceramides, betaines or oxygenated glycerol triesters, vitamin E, vitamin B12, EDTA, cetyl pyridinium chloride, chlorhexidine, other antiseptics, or combinations thereof.
12. The composition according to clause 10, wherein the preservatives are a combination of at least CPC, vitamin E, paraben.
13. The composition according to clause 10, wherein the composition comprises from 1 wt-% to 35 wt-% sweeteners based on the total weight of the composition.
14. The composition according to clause 10, wherein the composition comprises from 2.5 wt-% to 40 wt-% humectants based on the total weight of the composition.
15. The composition according to clause 11, wherein the composition does not include any quaternary antimicrobial compounds.
16. The composition according to any of clause 1 to 9, wherein the composition has a viscosity that renders it useful or deliverable as a sprayable composition.
17. The composition according to any of clause 1 to 9, wherein the composition remains physically stable and does not separate into water and oil phases when subjected to normal room temperature conditions, when subjected to temperatures approaching or surpassing the freezing point of the composition and subsequently thawed, or combinations thereof
18. The composition according to any of clause 1 to 9, wherein the composition can prevent, inhibit, disrupt, or any combination thereof the formation or maintenance of a biofilm in an area contacted with the composition.
19. The composition according to any of clause 1 to 9, wherein the composition can affect hydration loss in an area contacted by the composition.
20. The composition according to any of clause 1 to 9, wherein the composition can increase lubricity or lubriciousness of an area contacted by the composition.
21. A method of preventing, inhibiting, disrupting, or any combination thereof the formation or maintenance of a biofilm in an oral tissue, the method comprising contacting an oral tissue with a composition according to clause 18.
22. A method of decreasing hydration loss in an oral tissue, the method comprising contacting an oral tissue with a composition according to clause 19.
23. A method of affecting lubricity or lubriciousness in an oral tissue, the method comprising contacting an oral tissue with a composition according to clause 20.
24. A method of affecting the effects of xerostomia, dry mouth, or both, the method comprising contacting an oral tissue with a composition according to any of clauses 1 to 9.

Thus, embodiments of oral compositions and methods of use are disclosed. The implementations described above, and other implementations are within the scope of the following claims. One skilled in the art will appreciate that the present disclosure can be practiced with embodiments other than those disclosed. The disclosed embodiments are presented for purposes of illustration and not limitation.

What is claimed is:

1. A method of reducing one or more symptoms associated with one or more of xerostomia and dry mouth, the method comprising:
contacting an oral tissue with an edible oil-in-water composition,
the edible oil-in-water composition comprising:
an oil phase comprising:
one or more plant-based oils present in a total amount from 5 wt-% to 30 wt-% based on the total weight of the edible oil-in-water composition;
an aqueous phase comprising:
water,
wherein the aqueous phase is present in an amount from 70 wt-% to 95 wt-% based on the total weight of the edible oil-in-water composition;
one or more polyglycerol ester surfactant present in a total amount from 0.1 wt-% to 2 wt-% based on the total weight of the edible oil-in-water composition,
viscosity modifiers present in a total amount from 0.05 wt % to 3 wt-% based on the total weight of the composition,
wherein at least one viscosity modifier is ethyl cellulose, and
wherein at least one viscosity modifier is selected from hydroxypropyl guar and xanthan gum,
wherein the edible oil-in-water composition is characterized by a pH from 4.5 to 9.5.

2. The method of claim 1, the edible oil-in-water composition comprising xanthan gum present in an amount from 0.5 wt % to 0.7 wt % based on the weight of the aqueous phase.

3. The method of claim 1, wherein the viscosity modifiers are present in an amount not less than 0.2 weight percent based on the total weight of the edible oil-in-water composition.

4. The method of claim 1, wherein the edible oil-in-water composition further comprises fish oil.

5. The method according to claim 1, wherein the edible oil-in-water composition further comprises sweeteners, humectants, mineral salts, remineralizing agents, caries preventing agents, buffering components, flavorants, preservative agents, or a combination thereof.

6. The method of claim 1, wherein the edible oil-in-water composition comprises at least 2 wt % ethyl cellulose based on the weight of the oil phase, and 0.5 wt % to 0.7 wt % of hydroxypropyl guar or xanthan gum or based on the weight of the aqueous phase.

7. The method according to claim 1, the edible oil-in-water composition further comprising a viscosity modifier selected from fumed silica, wherein the fumed silica is present in an amount not less than 0.5 wt-% based on the total weight of the edible oil-in-water composition.

8. The method according to claim 1, the polyglycerol ester is selected from polyglyceryl-10 stearate, polyglyceryl-10 dipalmitate, polyglyceryl-6-distearate, polyglyceryl-10 oleate, polyglyceryl-10 caprylate/caprate, and a combination thereof.

9. The method according to claim 1, wherein the one or more edible plant based oils are selected from: sunflower oil, safflower oil, olive oil, coconut oil, palm oil, peanut oil, soybean oil, linseed oil, rapeseed oil, flaxseed oil, hempseed oil, cocoa butter, walnut oil, corn oil, grape seed oil, sesame oil, groundnut oil, wheat germ oil, cottonseed oil, watermelon seed oil, lemon oil, orange oil, thistle oil, tomato seed oil, almond oil, *perilla* oil, canola oil, pistachio oil, hazelnut oil, and avocado oil.

10. The method according to claim 1, wherein the one or more edible plant-based oils are present in an amount from 10 wt-% to 25 wt-% based on the total weight of the edible oil-in-water composition.

11. The method according to claim 10, wherein the one or more edible plant-based oils are present in an amount from 15 wt-% to 22 wt-% based on the total weight of the edible oil-in-water composition.

12. The method of claim 5, wherein the edible oil-in-water composition further comprises a remineralizing agent selected from calcium chloride.

13. The method according to claim 1, wherein the edible oil-in-water composition further comprises aloe vera, folic acid, hyaluronic acid, ceramides, betaines or oxygenated glycerol triesters, vitamin E, vitamin B12, EDTA, cetyl pyridinium chloride, chlorhexidine, other antiseptics, or a combination thereof.

14. The method according to claim 5, wherein the preservative agents are a combination of at least CPC, vitamin E, paraben.

15. The method according to claim 5, wherein the edible oil-in-water composition further comprises a sweetener present in an amount from 1 wt-% to 35 wt-% based on the total weight of the edible oil-in-water composition.

16. The method according to claim 5, wherein the edible oil-in-water composition further comprises a humectant present in an amount from 2.5 wt-% to 40 wt-% based on the total weight of the edible oil-in-water composition.

17. The method according to claim 13, wherein the edible oil-in-water composition excludes quaternary antimicrobial compounds.

18. The method according to claim 1, wherein the edible oil-in-water composition is characterized by a viscosity effective for use as a sprayable composition.

19. The method according to claim 1, wherein the edible oil-in-water composition remains physically stable and does not separate into water and oil phases when subjected to normal room temperature conditions, when subjected to temperatures approaching or surpassing the freezing point of the edible oil-in-water composition and subsequently thawed, or combinations thereof.

20. The method according to claim 1, wherein the edible oil-in-water composition reduces hydration loss in an area contacted by the edible oil-in-water composition.

21. The method according to claim 1, wherein the edible oil-in-water composition increases lubricity or lubriciousness of an area contacted by the edible oil-in-water composition.

* * * * *